(12) United States Patent  
Ajay et al.

(10) Patent No.: US 8,892,399 B2  
(45) Date of Patent: **\*Nov. 18, 2014**

(54) SENSING APPARATUS AND METHOD

(75) Inventors: Kemal Ajay, Mount Waverley (AU); Arjun Vinoo Caprihan, Saint Helena (AU); Michael Rezny, Mount Waverley (AU)

(73) Assignee: XTralis Technologies Ltd, Sydney (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/544,214

(22) Filed: Jul. 9, 2012

(65) Prior Publication Data

US 2013/0013227 A1 Jan. 10, 2013

Related U.S. Application Data

(63) Continuation of application No. 10/556,482, filed as application No. PCT/AU2004/000639 on Dec. 14, 2006, now Pat. No. 8,224,621.

(30) Foreign Application Priority Data

May 14, 2003 (AU) ................................ 2003902318

(51) Int. Cl.  
*G06F 3/02* (2006.01)  
*G01G 3/15* (2006.01)  
(Continued)

(52) U.S. Cl.  
CPC ...... *G08B 17/10* (2013.01); *G01N 2291/02836* (2013.01); *G01N 2015/0046* (2013.01); *G01N 2291/02408* (2013.01); *G01F 1/667* (2013.01); *G01N 1/2205* (2013.01); *G01N 2291/0217* (2013.01); *G01N 1/2273* (2013.01); *G01N 2015/1486* (2013.01); *G01N 1/26* (2013.01); *G01N 29/024* (2013.01)

USPC ............ 702/176; 702/175; 702/179; 702/189

(58) Field of Classification Search  
USPC ............... 702/14, 36, 59, 182, 183, 186, 189; 73/40; 381/159; 340/630  
See application file for complete search history.

(56) References Cited

U.S. PATENT DOCUMENTS 5,052,230 A 10/1991 Lang et al.  
5,103,212 A * 4/1992 Notarianni et al. ........... 340/628  
(Continued)

FOREIGN PATENT DOCUMENTS

DE 3331203 A1 8/1983  
DE 4400363 A1 1/1994  
(Continued)

OTHER PUBLICATIONS

IDS foreign Reference from applicant, Schoenfelder et al., Smoke detector with aspiration unit and flow sensor, Feb. 12, 1999, European Patent Application, pp. 1-14. European Patent Application EP 1 006 500 A2.*

(Continued)

*Primary Examiner* — Eliseo Ramos Feliciano  
*Assistant Examiner* — Felix Suarez  
(74) *Attorney, Agent, or Firm* — Sughrue Mion, PLLC

(57) ABSTRACT

A method of detecting one or more blocked sampling holes in a pipe of an aspirated smoke detector system. The method includes ascertaining the base flow of fluid through a particle detector using a flow sensor; monitoring subsequent flow through the particle detector; comparing the subsequent flow with the base flow; and indicating a fault if the difference between the base flow and the subsequent flow exceeds a predetermined threshold.

9 Claims, 32 Drawing Sheets

(51) Int. Cl.
*G06F 3/03* (2006.01)
*H04B 13/02* (2006.01)
*G01F 1/66* (2006.01)
*G01N 1/22* (2006.01)
*G01N 1/26* (2006.01)
*G08B 17/10* (2006.01)
*G01N 29/024* (2006.01)
*G01N 15/00* (2006.01)
*G01N 15/14* (2006.01)

(56) References Cited

U.S. PATENT DOCUMENTS

| | | | |
|---|---|---|---|
| 5,131,052 A * | 7/1992 | Hill et al. | 381/336 |
| 5,150,310 A | 9/1992 | Greenspun et al. | |
| 5,163,331 A | 11/1992 | Gill | |
| 5,178,018 A | 1/1993 | Gill | |
| 5,178,606 A | 1/1993 | Ognier et al. | |
| 5,388,445 A * | 2/1995 | Walters et al. | 73/40.5 R |
| 5,533,408 A | 7/1996 | Oldenziel et al. | |
| 5,917,417 A * | 6/1999 | Girling et al. | 340/628 |
| 5,926,098 A * | 7/1999 | Wiemeyer et al. | 340/630 |
| 6,062,091 A | 5/2000 | Baumoel | |
| 6,133,839 A | 10/2000 | Ellul, Jr. et al. | |
| 6,166,648 A | 12/2000 | Wiemeyer et al. | |
| 6,178,827 B1 | 1/2001 | Feller | |
| 6,338,028 B1 | 1/2002 | Shelton et al. | |
| 6,351,999 B1 | 3/2002 | Maul et al. | |
| 6,408,704 B1 * | 6/2002 | Willeke | 73/865.5 |
| 6,871,148 B2 | 3/2005 | Morgen et al. | |
| 7,270,001 B2 | 9/2007 | Betz | |
| 8,224,621 B2 * | 7/2012 | Ajay et al. | 702/176 |

FOREIGN PATENT DOCUMENTS

| | | |
|---|---|---|
| EP | 0197371 A1 | 3/1986 |
| EP | 1006500 A2 | 6/2000 |
| GB | 2344175 A | 5/2000 |
| JP | 11-287817 A | 10/1999 |
| JP | 2000-035353 A | 2/2000 |
| JP | 2000163672 A | 6/2000 |
| JP | 2001091383 A | 4/2001 |
| JP | 2001250175 A | 9/2001 |
| JP | 2002-81986 | 3/2002 |
| JP | 2007222813 A | 9/2007 |
| JP | 2007325151 A | 12/2007 |
| JP | 2008202970 A | 9/2008 |
| JP | 2009196843 A | 9/2009 |
| WO | WO 88/08516 A1 | 11/1988 |
| WO | WO 00/43736 A1 | 7/2000 |
| WO | WO 03/102512 A1 | 12/2003 |

OTHER PUBLICATIONS

European Search Report issued in European Application N. 10 011 484.2 dated Mar. 1, 2011 (6 pages).
European Communication for Application No. 04732876.0; Mar. 19, 2012.
Japanese Office Action for JP2010257936 (English Summary only).

* cited by examiner

SENSING APPARATUS AND METHOD

RELATED APPLICATIONS

This application is a continuation application of U.S. patent application Ser. No. 10/556,482, filed Nov. 14, 2005, now U.S. Pat. No. 8,224,621 issued on Jul. 17, 2012, which is a 371 of PCT/AU04/00639, filed May 14, 2004, which claims priority to Australian Provisional Patent Application no. 2003902318, filed 14 May 2003 and entitled "Improved Sensing Apparatus and Method" and, the specification thereof is incorporated herein by reference in its entirety and for all purpose.

FIELD OF INVENTION

The present invention relates to the field of sensing apparatus. In particular, the present invention relates to an improved particle detector and method for detecting particles in air. In one form, the invention relates to an improvement in particle detectors and an associated method of detecting particles in air sampled from a number of locations. It will be convenient to hereinafter describe the invention in relation to the use of an ultrasonic means of flow sensing within an aspirated smoke detector system, however, it should be appreciated that the present invention may not be limited to that use, only.

RELATED ART

The inventor has identified the following related art. Particle detectors are useful in detecting smoke particles in an airstream as a means of determining whether a location may contain a thermal event. Sensitive smoke detectors, such as the VESDA™ LaserPlus™ smoke detector sold by Vision Fire and Security Pty Ltd, detect the number of particles in an airstream. Typical thermal events, such as combustion, produce significant quantities of airborne particles, and therefore detecting these particles is useful in determining whether there may be a thermal event in a particular location. One type of smoke detector system uses a sampling network of pipes, each pipe having a number of apertures along its length. The pipe network is connected to a particle detector, and an aspirator draws air through the pipes and into a particle detecting chamber. Using a pipe network, air may be sampled from a number of different points over an area. To maintain and improve upon the efficiency and effectiveness of an aspirated smoke detector system, it is desirable to determine flow through the pipe network. By way of example, flowmeters suitable for determining the flow of a fluid, ordinarily in liquid state, through a fluid carrying pipe are disclosed in the following references.

WO 88/08516 (Micronics Limited), entitled "Ultrasonic Fluid Flowmeter" discloses a non-intrusive ultrasonic flowmeter operating on the principle of time-of-flight measurement, comprising a first mounting block having a first fixed transducer being oriented to direct an ultrasonic pulse at an angle to the axis of fluid flow in a pipe. A second transducer within the first mounting block is angled to direct an ultrasonic pulse in a direction perpendicular to the axis of flow. A third transducer is fixed within a second block at a distance from the first block and is oriented to intercept the direct or reflected acoustic path of a pulse transmitted by the first transducer. An empirical calculation of the time of flight of the pulse from the first to the third transducers is carried out using direct output signals from the transducers, which allows for a determination of the flow rate of the fluid. However, this empirically determined flow rate is not accurate and is corrected for variation in the propagation rate of the transmitted ultrasound pulses by deriving a correlation factor from the output signal of the second transducer.

U.S. Pat. No. 5,052,230 (Lang et al), entitled "Method and Arrangement for Flow Rate Measurement by Means of Ultrasonic Waves" discloses a method and apparatus for determining the flow rate of a liquid in a measuring tube which comprises digitally measuring the total phase shift that will naturally occur between a transmitted waveform and a received waveform of an ultrasonic signal being transmitted and having to travel a distance before it is received within an arrangement comprising two transducers spaced apart on the measuring tube. According to Lang et al, the flow velocity is first determined using known values of the frequency of the ultrasonic wave and the distance between the two transducers and by calculating the difference between the total phase shifts obtained in relation to the ultrasonic signal propagated firstly in the direction of flow and then against the direction of flow. The flow rate of the liquid is then determined by multiplying the determined flow velocity by the known flow cross-sectional area of the measuring tube. Lang et al recognises that the total angular phase shift between a transmitted and received ultrasonic signal is made up of the number of whole wavelengths of the ultrasonic signal between the two transducers and any residual phase angle. The method and apparatus of Lang et al therefore provides a two part solution in which a first arrangement is used to determine the number of whole wavelengths disposed in the measuring tube and, a second arrangement is used to determine the residual or exact phase angle between the transmitted and received signal. It is noted that Lang et al uses digital pulse counting techniques to determine measurement intervals in each part of its two part solution and discloses improvements to the pulse counting accuracy in each part of the disclosed solution. In the whole wavelength determination full wave rectification of the received signal is performed in order to have the received signal exceed a threshold for stopping the pulse counter earlier than an unrectified signal. In the residual phase angle determination, firstly the start phase of a counting frequency signal is varied at the beginning of each counting operation to overcome quantization errors and secondly, where very small residual angles are detected, the digital equivalent of either the transmitted or received signal is inverted thereby adding 180° to the phase angle and thus the duration of a measuring pulse is correspondingly longer for greater resolution. The phase inverting step requires a corresponding delay to be introduced to the non-inverted signal, ether the received or transmitted signal, in order to compensate for the delay caused by the inverter. The whole wavelength determination is limited by an accurate determination of the onset of the arrival of the received ultrasonic signal.

U.S. Pat. No. 5,533,408 (Oldenziel et al), entitled "Clamp-On Ultrasonic Volumetric Flowmeter"; discloses a dual mode clamp-on ultrasonic volumetric flowmeter comprising at least one pair of ultrasonic transducers on the outside surface of a pipe carrying a fluid to be measured in which a time-of-flight measurement principle or a correlation technique are selected depending on whether foreign particles are present in the fluid. Oldenziel et al discloses an improvement in which based on a threshold signal derived from an integrated signal of one of the transducers, a user may preset or select a foreign particle content in the fluid at which to changeover from travel time measurement to correlation measurement, U.S. Pat. No. 6,351,999 (Maul et al), entitled "Vortex Flow Sensor" discloses a sensor for measuring flow velocity and/or flow rate of a fluid in which turbulent flow is introduced into the fluid by way of a bluff body fixedly disposed along a tube diameter for generating Karman vortices, whose frequency is proportional to the fluid flow velocity. The sensor disclosed by Maul et al is an optical sensor system comprising a laser differential interferometer.

A method and apparatus of more general application is disclosed in U.S. Pat. No. 5,983,730 (Freund et al), entitled "Method and Apparatus for Measuring the Time of Flight of a Signal". Freund et al is directed to the problem of accurately measuring the time of flight of a signal in particular applications where the precision of less than one period of the signal is required such as in flow, level, speed of sound and acoustic impedance measurements. Accordingly, Freund et al discloses a method and apparatus comprising the steps of receiving a transmitted signal and detecting the onset of the signal as it arrives by way of performing a set of operations upon the received signal to provide a discriminated received signal having a critical point that may be used to determine the time of flight of the transmitted signal. The intensive signal processing operations of Freund et al concentrate on the received signal. Freund et al does not disclose any processing operations for the signal as it is transmitted nor any treatment of the transmitted signal waveform before it is received.

U.S. Pat. No. 5,178,018 (Gill) discloses a measurement system for measuring the time for a signal to pass between two transducers to allow the determination of the fluid flow of a gas, as in a gas meter for example. A signal with a phase change acts as a marker, which is transmitted from one transducer and received by another transducer. On receipt, the phase change marker is detected and is used in conjunction with corresponding amplitude information in the received signal to calculate a time of travel of the signal and hence flow rates of the fluid. The system of Gill requires very high bandwidth transducers along with expensive and powerful drive circuitry in order to provide sufficient signal output to overcome background and other noise within flow systems. It is also noted that transducer temperature changes alter the phase and frequency response of the transducers.

Any discussion of documents, devices, acts or knowledge in this specification is included to explain the context of the invention. It should not be taken as an admission that any of the material forms a part of the prior art base or the common general knowledge in the relevant art in Australia or elsewhere on or before the priority date of the disclosure and claims herein.

SUMMARY OF INVENTION

In one aspect the present invention provides a method of determining the time of flight of a signal transmitted between a transmitter and a receiver, said method comprising the steps of:

transmitting a first signal comprising at least one characteristic waveform feature;

transmitting a second signal comprising at least one characteristic waveform feature and a waveform modification introduced at a predetermined point in time of the duration of the second signal;

receiving said first and second transmitted signals;

determining a point of diversion between corresponding characteristic waveform features of the first and second received signals comprising super positioning said first and second received signals such that said point of diversion corresponds to an arrival time of the introduced waveform feature modification at the receiver.

The determined point of diversion advantageously resolves ambiguities associated with similar characteristic features cyclically present in the received waveform. In other words, the characteristic feature of a signal generated at the transmitter which corresponds to the predetermined point in time at which the waveform modification is introduced may be clearly distinguished from other such characteristic features that may recur cyclically throughout the transmitted signal. Once a point of diversion of a second signal of the modified type with respect to a first signal of the unmodified type is determined at the receiver then this point in time may be confidently determined as the time of arrival of not only the received signal burst but the arrival time of a specific portion of the signal burst with a resolution of less than a single cycle within the burst and being of the order of the duration of a characteristic waveform feature.

In essence the present invention stems from the realisation that a determination of the arrival time of a signal is readily ascertained when a signal with a portion specifically modified is overlaid in time relative to an unmodified signal. This solution obviates the need for sophisticated electronics used to find a predetermined marker buried within a given received signal transmission, which manifests itself as an unpredictable received signal waveform distortion that is also subject to further distortions due to system and component noise, instabilities and other uncertainties. By making a relative measurement at the receiver, the present invention cancels these distortions and uncertainties to the extent that the only diversion manifested between a second modified and a first unmodified signal is the introduced waveform modification of the second signal placed, as it may be, at a predetermined location of the second signal for ease of timing reference.

In the preferred embodiment, once the diversion point is used to unambiguously determine the time of flight of the received signal, the characteristic feature of the first unmodified signal corresponding to the location of the diversion point may be subsequently used to guide the selection and measurement of a characteristic waveform feature of a plurality of transmitted signals of the first unmodified signal type without further reference to the diversion point. This characteristic feature of the first signal type may thereafter be tracked in subsequent unmodified signals to allow for variations due to flow, temperature and other physical effects.

In another aspect the present invention provides apparatus adapted to determine the time of flight of a signal transmitted between a transmitter and a receiver, said apparatus comprising:

processor means adapted to operate in accordance with a predetermined instruction set, said apparatus, in conjunction with said instruction set, being adapted to perform the method of determining the time of flight of a signal transmitted between a transmitter and a receiver as disclosed herein.

In yet another aspect the present invention provides a method of monitoring flow through a particle detector of an aspirated smoke detector system, the method comprising the steps of:

ascertaining the base flow of fluid through a particle detector using a flow sensor;

monitoring subsequent flow through the particle detector;

comparing the subsequent flow with the base flow, and indicating a fault if the difference between the base flow and the subsequent flow exceeds a predetermined threshold wherein base flow and subsequent flow are determined at respective times according to the following general flow calculation:

$$f = s \times A$$

where f=volumetric flow;

A=cross sectional area of an air flow path through the detector system;

s=speed of air through the detector system such that s is given by;

$$s = \frac{d}{2}\left(\frac{1}{t_2} - \frac{1}{t_1}\right)$$

where $t_1$ is the transit time of a signal transmitted in a forward direction, being generally in the direction of flow, from a first transducer located adjacent the flow path to a second transducer located generally opposite the first transducer and adjacent the flow path;

$t_2$ is the transit time of a signal transmitted in a reverse direction, being generally against the direction of flow, from the second transducer to the first transducer;

d is a distance travelled by the signal between the first and second transducer;

and wherein both $t_1$ and $t_2$ are determined in accordance with a method of determining the time of flight of a signal transmitted between the first transducer acting as a transmitter and the second transducer acting as a receiver as disclosed herein.

In still another aspect the present invention provides apparatus adapted to monitor flow through a particle detector of an aspirated smoke detector system, said apparatus comprising:

processor means adapted to operate in accordance with a predetermined instruction set, aid apparatus, in conjunction with said instruction set, being adapted to perform a method of monitoring flow through a particle detector of an aspirated smoke detector system as disclosed herein.

In yet a further aspect the present invention provides a method of determining the time of flight of a signal transmitted between a transmitter and a receiver, said method comprising the steps of:

a) transmitting a first and a second signal, where both signals comprise at least one characteristic waveform feature and the second signal further comprises a waveform modification introduced at a predetermined point in time of the duration of the second signal;

b) receiving said first and second transmitted signals;

c) scanning through said received signals in time to determine a point of diversion between corresponding characteristic waveform features of the first and second received signals, wherein said point of diversion corresponds to a time of reception of the introduced waveform feature modification at the receiver.

In a preferred embodiment, the following steps are performed after the above scanning step as part of the determination of the point of diversion:

d) for each characteristic waveform feature of the first received signal calculating the difference between a value of the first received signal and a corresponding value of the second received signal;

e) designating the first point of occurrence at which the calculated difference is greater than the value of the second received signal as a point of diversion.

Similarly, in a preferred embodiment, at least one or more of the following steps are performed after the above designating step to determine the time of flight of a signal:

f) calculating the difference between the time of the point of diversion and the time of transmission of the introduced waveform feature modification;

g) measuring a time relationship between a nominated characteristic waveform feature and the point of diversion and calculating the difference between the time of reception and the time of transmission of the nominated characteristic waveform feature.

In an embodiment of the invention with respect to step g) described above, thereafter for subsequent transmitted first unmodified signals, the time of flight may be determined by calculating the difference between the time of reception and the time of transmission of the nominated characteristic waveform feature of the subsequent first signals without reference to the point of diversion. The nominated characteristic waveform feature may be locked onto and tracked to allow for variations in arrival time due to physical changes in the transport medium between transducers such as temperature, density etc.

In a preferred embodiment the present invention provides a method of determining the time of flight of a signal as herein disclosed which further comprises the steps of:

selecting a characteristic waveform feature of a first signal in accordance with predetermined selection criteria based on the point of diversion;

transmitting and receiving a plurality of first signals;

detecting zero-crossings of the received plurality of first signals which indicate the presence of the selected characteristic waveform feature in each of the received plurality of first signals;

estimating a position of the selected characteristic waveform feature of the received plurality of first signals in accordance with predetermined estimation criteria based on the detected zero-crossings to provide a position estimation value;

processing the position estimation value to determine a corresponding estimation time;

calculating the time of arrival of the selected characteristic waveform feature of at least one of the plurality of received first signals by adding a predetermined delay time to the estimation time.

In this preferred embodiment, the predetermined selection criteria may comprise one of:

a) adding a predefined delay to the time of the point of diversion;

b) subtracting a predefined delay from the time of the point of diversion.

Further, in the preferred embodiment the predetermined estimation criteria may comprise:

a) measuring the time of zero-crossings adjacent the selected characteristic waveform feature and;

b) averaging the measured time of zero-crossings.

The zero-crossings adjacent the selected characteristic waveform feature may occur on each side of the selected feature in time.

In the preferred embodiment the present invention provides apparatus adapted to determine the time of flight of a signal transmitted between a transmitter and a receiver, said apparatus comprising:

processor means adapted to operate in accordance with a predetermined instruction set, said apparatus, in conjunction with said instruction set, being adapted to perform the method of determining the time of flight of a signal as disclosed hereinabove wherein said apparatus comprises:

signal transducing means for transmitting and receiving a plurality of first signals;

waveform feature selection means operatively connected to the signal transducing means and the processor means for selecting a characteristic waveform feature of a first signal in accordance with predetermined selection criteria based on the point of diversion;

zero-crossing detection means operatively connected to transducing means and the processor means for detecting zero-crossings of the received plurality of first signals which indicate the presence of the selected characteristic waveform feature in each of the received plurality of first signals;

signal position estimation means operatively connected to the zero-crossing detection means and the processor means for estimating a position of the selected characteristic waveform feature of the received plurality of first signals in accordance with predetermined estimation criteria based on the detected zero-crossings to provide a position estimation value;

wherein the processor means processes the position estimation value to determine a corresponding estimation time and calculates the time of arrival of the selected characteristic waveform feature of at least one of the received plurality of first signals by adding a predetermined delay time to the estimation time.

The signal position estimation means may comprise a dual slope integrator. In an alternate embodiment, the received plurality of first signals are digitised and said processor means comprises digital data processing means comprising the zero-crossing detection means and the signal position estimation means.

In yet a further aspect the present invention provides a method of detecting one or more blocked sampling holes in a pipe of an aspirated smoke detector system comprising:

ascertaining the base flow of fluid through a particle detector using a flow sensor;

monitoring subsequent flow through the particle detector;

comparing the subsequent flow with the base flow, and indicating a fault if the difference between the base flow and the subsequent flow exceeds a predetermined threshold.

In another aspect the present invention provides an aspirated smoke detector comprising a particle detector, a sampling network and an aspirator, an inlet, an outlet and a flow sensor, wherein the flow sensor uses ultrasonic waves to detect the flow rate of air entering the particle detector.

In one embodiment of the present invention there is provided a computer program product comprising:

a computer usable medium having computer readable program code and computer readable system code embodied on said medium for monitoring flow through a particle detector of an aspirated smoke detector system within a data processing system, said computer program product comprising:

computer readable code within said computer usable medium for performing the method of monitoring flow through a particle detector of an aspirated smoke detector system as disclosed herein.

In another embodiment of the present invention there is provided a computer program product comprising:

a computer usable medium having computer readable program code and computer readable system code embodied on said medium for determining the time of flight of a signal transmitted between a transmitter and a receiver within a data processing system, said computer program product comprising:

computer readable code within said computer usable medium for performing the method of determining the time of flight of a signal transmitted between a transmitter and a receiver as disclosed herein.

In yet a further embodiment of the present invention there is provided a computer program product comprising:

a computer usable medium having computer readable program code and computer readable system code embodied on said medium for detecting one or more blocked sampling holes in a pipe of an aspirated smoke detector system within a data processing system, said computer program product comprising:

computer readable code within said computer usable medium for performing the method of detecting one or more blocked sampling holes of an aspirated smoke detector system as disclosed herein.

Other preferred forms, aspects and embodiments are disclosed in the specification and/or defined in the appended claims, forming a part of the description of the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Further disclosure, improvements, advantages, features and aspects of the present invention may be better understood by those skilled in the relevant art by reference to the following description of preferred embodiments taken in conjunction with the accompanying drawings, which are given by way of illustration only, and thus are not limiting to the scope of the present invention, and in which.

DETAILED DESCRIPTION

Figure 1:
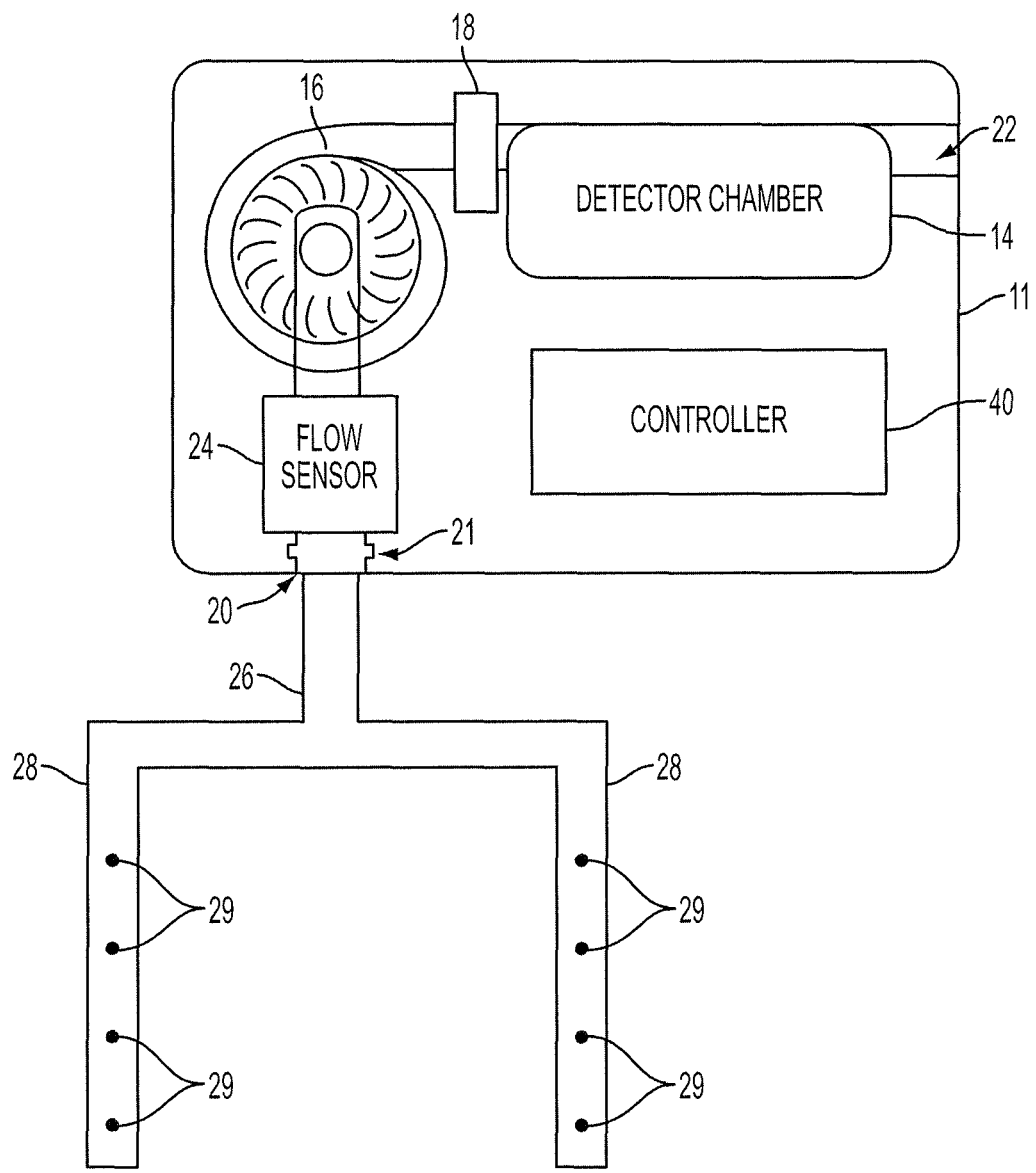
FIG. 1 shows a schematic arrangement of an embodiment of a sensing apparatus for a smoke detector system.

A particle detector system in the form of a smoke detector 10, shown in FIG. 1, comprises a housing 11 attached to a conduit or flow channel 26. The detector 10 has a number of component parts comprising a detector chamber 14, an aspirator 16, a filter 18, a fluid inlet 20 and a fluid outlet 22, For purposes of clarity the precise fluid flow path within the chamber 14 is not shown in FIG. 1.

Also associated with the smoke detector 10 is a flow sensor 24. In FIG. 1 the flow sensor 24 is in fluid communication with the inlet 20 and aspirator 16.

Conduit 26 is connected to a network of pipes 28. Each pipe 28 has a number of sampling points 29, which may comprise holes. The sampling points 29 allow air to be sampled at various places in an area to be protected, such as a building (not shown). The aspirator 16 draws air into the sampling points 29 through the pipe network 28, through the inlet 20 and into the housing 11. The air sample then passes into the flow sensor 24. A flow disruptor 21 may be located upstream of the flow sensor 24 to remove the laminar flow characteristics of steady air flow through the pipe network.

The aspirator 16 in the detector 10 draws the sampled air along the pipes 28, through the inlet 20, flow disruptor 21, flow sensor 24 and into the detector chamber 14, where the particles are detected. If the level of particles exceeds a predetermined level, then the detector 10 may take a number of actions, such as setting off an alarm, activating fire suppression systems or other activities. The detector 10 is typically in communication with external devices such as a fire panel (not shown). This system may be employed in a number of buildings, and a typical system would be a VESDA1™ Laser Plus™ smoke detector system as sold by Vision Fire and Security Pty Ltd, attached to a pipe network.

Figure 2:
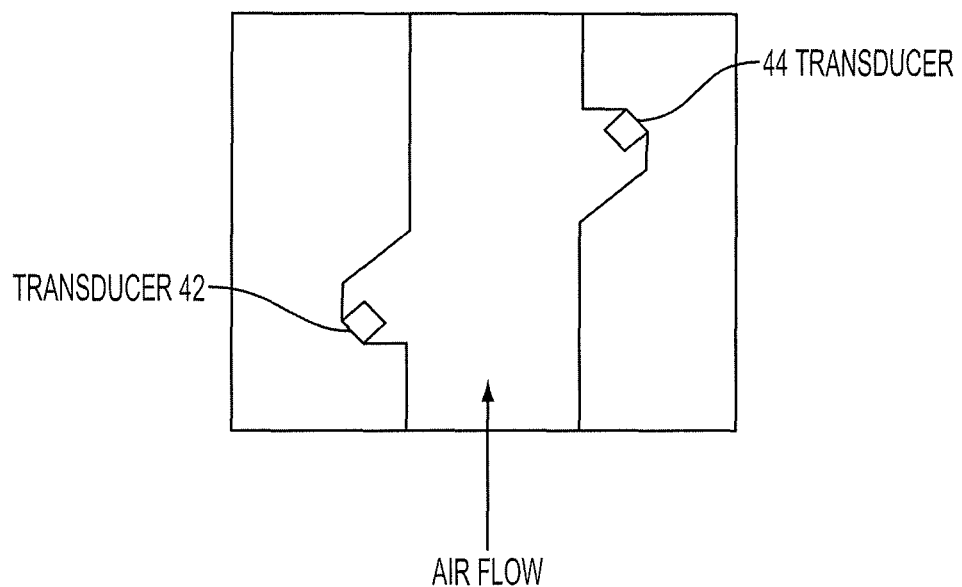
FIG. 2 shows a schematic of an embodiment of a flow sensor arrangement for a sensing apparatus as shown in FIG. 1.
Figure 4:
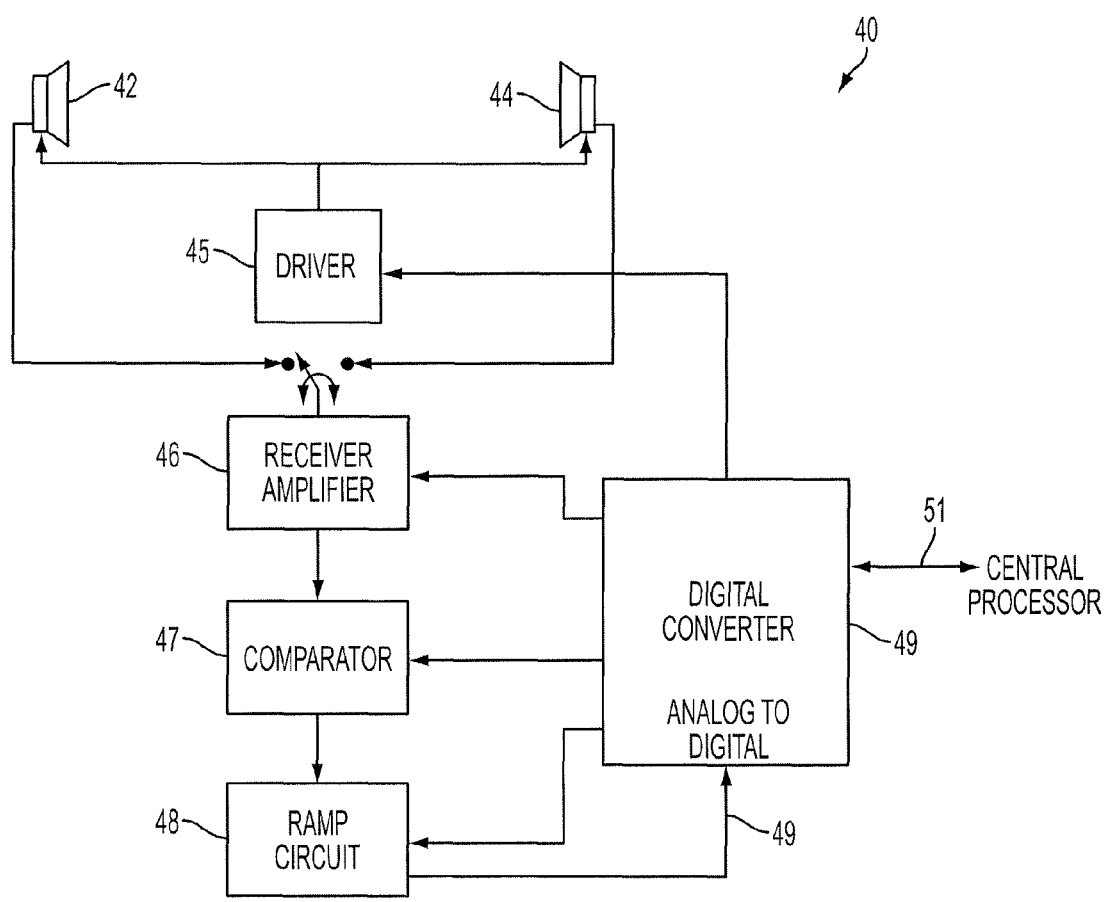
FIG. 4 shows a schematic of the circuit components of a controller and flow sensor of the sensing apparatus of FIG. 1.

FIG. 2 illustrates the flow sensor as an offset arrangement comprising two ultrasonic transducers 42, 44 placed on alternate sides of an air flow path and displaced in the direction of flow. In one embodiment, the flow sensor 24 in the form of an ultrasonic flow sensor has two combined receiver/transmitters, such as the US80KS-01 as sold by Measurement Specialties Inc. Each combined receiver/transmitter is a piezoelectric transducer connected to a controller 40. Referring to FIG. 4, the controller 40 comprises a driver 45 acting as a wave or signal generator and receiver 46, analog to digital converter 49 and a digital microprocessor 50, which may have connection to a central processor system or network facility via a suitable connection such as a serial data link 51. The controller 40 generates a signal in a first direction by exciting transducer 42 via driver 45, generating an ultrasonic acoustic signal, which is received by transducer 44, then a signal in a second direction by exciting transducer 44 via driver 45 generating an ultrasonic signal which is received by transducer 42. The microprocessor 50, in conjunction with the receiver circuitry 46 measures the time taken for the signals to propagate in each direction.

Although the flow calculated by this method does not account for travel time of the signal through air, which is not directly in the flow path, for example the dead space directly in front of each transducer and outside the flow path, this may be corrected for if necessary by a constant multiplying factor as would be recognised by the person skilled in the art. Notwithstanding such a correction, the following calculation applies in carrying out a flow determination in accordance with an embodiment of the present invention.

For a propagation time in the first direction of $t_1$ and a propagation time in the second direction of $t_2$, the speed of the air flow past the transducers may be calculated as:

$$s = \frac{d}{2}\left(\frac{1}{t_2} - \frac{1}{t_1}\right)$$

where s is the speed of the air and of is the distance between the transducers. It is then a simple matter to determine flow based on a calculation given the cross-sectional area A of the flow path. That is, flow f is $$f = A\frac{d}{2}\left(\frac{1}{t_2} - \frac{1}{t_1}\right)$$

It is possible to determine the propagation time in each of the two aforementioned directions by a number of means, an example of such means being the use of a high-speed electronic digital counter which is triggered by the application of the exciting voltage to the transmitting transducer and halted by the arrival of the received ultrasonic signal at the receiving transducer.

In a further embodiment a digital signal processor may be used to sample the received signal using an analog to digital converter and to then calculate the precise arrival time of a signal by detecting a characteristic feature in the received signal, namely, a waveform characteristic or attribute such as, a peak, or combination of peaks or a zero crossing or combination of zero crossings. Advantageously, embodiments of the present invention introduce a predetermined artefact or modification to the transmitted waveform in a manner, which allows a marked differentiation between a received waveform with and without the introduced artefact, which provides a stable point of reference for determining the time of arrival of the received signal. Preferably, the introduced artefact to the waveform characteristic may be the result of a phase inversion provided in a cycle of the transmitted signal as described in more detail below.

The introduced waveform modification is introduced at a specified point in the duration of a reference signal to distinguish it from a normal unmodified signal. Preferably, the point in the signal duration chosen is one that readily allows determination of the signal's arrival at a receiver. If the transmitted signal comprises a pulse waveform then its duration is given by, the interval between (a) the time, during the first transition or cycle, that the pulse amplitude reaches a specified fraction (level) of its final amplitude, and (b) the time the pulse amplitude drops, on the last transition, to the same level, as would be understood by the person skilled in the art.

The flow sensor 24 is required in order to determine that the air-sampling pipe network 28 is in good order. In a first case, a high flow level indicates that pipe work has become dislodged from the smoke detector system 10 or has been broken whereas in a second case, a low flow level indicates some form of pipe blockage. In either of the aforementioned cases, it is likely that the performance of the smoke detection system 10 has become impaired so these conditions should be detected and reported so that corrective measures may be enacted.

Determining the rate of flow through a pipe network 28 is often difficult, and many known types of flow sensor require some part of the sensor to protrude into the airflow. The air sampled in a smoke detection system often contains contaminants for example in the form of particles and fibres. These contaminants may cause errors in the flow sensing means of related art mechanisms. For example, in resistive type devices, such as a constant temperature probe, accumulation of contaminants on the probe changes its heat transfer characteristics. Other flow sensors such as moving vane types also project into the air stream flowing through the pipe or housing of the detector and are also subject to contamination. Smoke detecting systems may be required to be situated in the field for many years without calibration, and therefore reliable flow sensing is important. Further, smoke detectors are ordinarily required to operate in a variety of conditions, such as a range of temperatures, humidities and pollution levels. These conditions may affect the performance of the flow meter, affecting the overall performance of the detector.

In other related art mechanisms, a restriction, such as an orifice or venturi, may be interposed within the flow path. A manometer may be used to measure the pressure drop across this restriction, which indicates the level of flow. This approach has the disadvantage that it impedes the flow of air and therefore reduces the efficiency of the aspirator causing excessive air transport time delays or reduced area coverage of the sampled smoke detection system overall. Such systems may also be subject to contamination problems as the restriction accumulates dust, fibres and other matter, causing the flow reading to drift from its correct value.

Further, most related art mechanisms measure the mass-flow of air, which is highly sensitive to density variations with temperature and altitude. Thus, such mechanisms require a compensation means for temperature and pressure in accordance with their individual characteristics incurring extra expense and calibration time. The present invention measures volumetric flow, which is substantially constant with temperature and is a better measure of pipe work blockage or disconnected pipe work.

In accordance with embodiments described herein, using an ultrasonic flow sensing mechanism within a smoke detection system, at least one or more of the above described deficiencies may be overcome.

The present invention has been found to result in a number of advantages, particularly for sensing air flow in a smoke detector system, such as:

a. Ultrasonic flow sensing reports volumetric air flow (liters per minute or equivalent) and is not dependent of pressure or density;

b. The transducers are placed outside the airflow path so airborne contaminants are not deposited on the transducers;

c. The system has no moving parts and so is not subject to mechanical wear;

d. Ultrasonic flow sensing is intrinsically very stable allowing more sensitive detection of flow changes; and e. A measurement of air flow may be obtained with a high level of confidence given the accuracy of determination of the time of flight of an ultrasonic signal between a transmitting transducer and a receiving transducer where the time of arrival of the signal at the receiving transducer is determined in accordance with embodiments described herein.

One major problem of aspirated smoke detector systems is blocking of air flow, for example, in sample holes 29. It has been very difficult to detect whether one or more sampling holes 29 are blocked. Traditionally this has been addressed by visually checking the sample holes 29 or regular cleaning, whether required or not. Using an ultrasonic flow sensor 24 it is possible to detect smaller changes in airflow into the detector. As one or more sample holes 29 become blocked, the airflow into the detector drops, and the ultrasonic flow sensor 24 detects this. Once the flow of air drops below a predetermined value, the detector may indicate a fault, allowing a user to check the pipe network 28 and sampling holes 29 for blockage.

Figure 6:
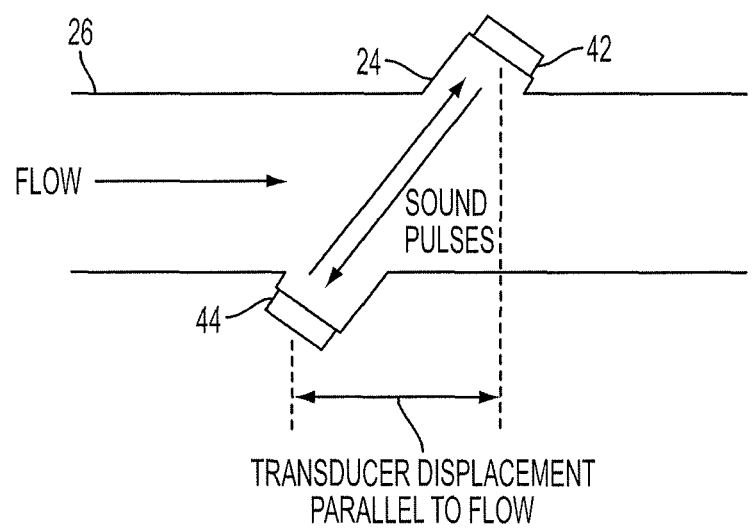
FIG. 6 shows an embodiment of a flow sensor arrangement in which time-of-flight measurements are performed.

In the preferred embodiment of the invention, an ultrasonic flow sensor 24 is interposed in the air flow path in order to detect any off-normal air flow condition in the air-sampling pipe network 28 of a smoke detector system 10. In the preferred embodiment, the flow sensor 24 comprises at least two transducers mounted on opposite sides of an air flow path and offset by a distance in the direction of flow as shown in FIGS. 2 and 6.

A control unit 40, shown in FIG. 4, comprising a driver stage 45, a receiver amplifier 46, a detector comprising comparator 47 and dual slope integrator 48 and microcontroller 50 is incorporated to initiate the excitation of a transmitting transducer 42 or 44 and to measure the propagation time of the ultrasonic signal to the receiving transducer 42 or 44.

Figure 5:
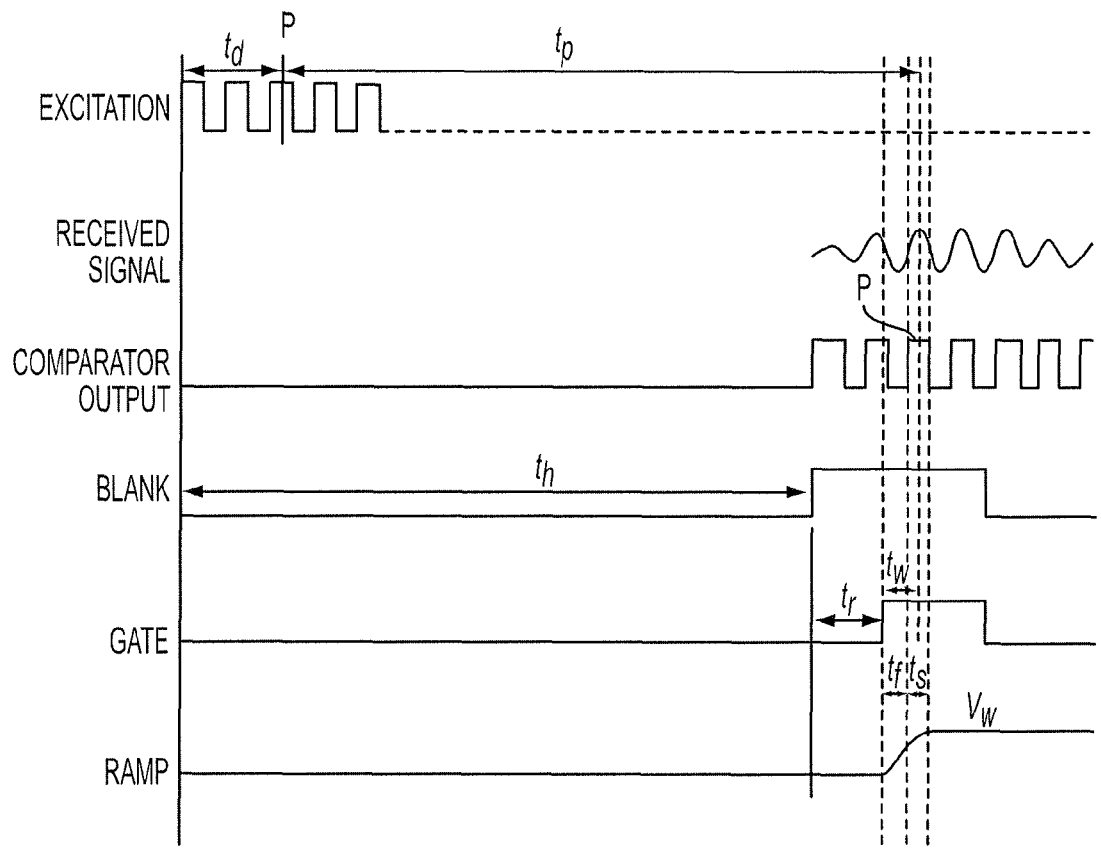
FIG. 5 shows the waveforms of signals received by the flow sensor of the sensing apparatus of FIG. 1.

In the preferred embodiment and with reference to FIG. 5, the microprocessor 50 is programmed to excite a transducer 42 or 44 with five pulses whose repetition rate is 80 kHz. The processor 50 is then required to wait for a known blanking time period $t_b$, and then activate the zero-crossing detector circuit. After a further time, $t_r$, which nominally corresponds to the expected occurrence of, for instance, the third peak of the received signal, the detector circuit is activated and using a dual-slope integrating ramp circuit 48, determines the time position of the centre of one of the peaks in the received signal relative to the end of $t_r$. This time $t_w$ is represented by a voltage $V_w$ that is measured by the analog to digital converter 49 on the microprocessor 50. This voltage is converted to a time by the formula $$t_w = kV_w$$

where k is a constant readily calculated from the integrator circuit 48 component values.

Therefore the total propagation time, from a known peak P in the transmission waveform, to the corresponding pulse in the received waveform $t_p$ as indicated in FIG. 5, is $$t_p = t_b + t_r + t_w - t_d$$

where $t_d$ is the delay from the start of the waveform to a nominated peak P in the waveform.

An aspect of the preferred embodiment is that the propagation time measurement uses an early part of the received waveform; usually the third or fourth peak, to determine the arrival time of the pulse. This has the advantage of avoiding phase and amplitude errors caused by the arrival of echoes and higher order propagation modes, which are sensitive to temperature.

A further aspect of the preferred embodiment is the use of a dual slope integrator 48 to determine the location of the centre of the sinusoidal wave-peak P used for the receive timing. This aspect averages the leading and trailing zero crossing times of the nominated wave-peak P in order to estimate its centre time. This aspect allows the precise determination of the sinusoidal wave position at very low cost and avoids the need for high-speed counters or high speed sampling and processing schemes. This aspect is explained in more detail below with reference to the attached drawings.

The dual slope integrator 48 is a means of estimating the centre time point of a waveform event characterised by a rising edge followed by a falling edge or alternatively, a falling edge followed by a rising edge. For the purposes of clarity of explanation and with reference to FIGS. 3a and 3b, only the case of the rising edge followed by the falling edge will be discussed.

Figure 3A:
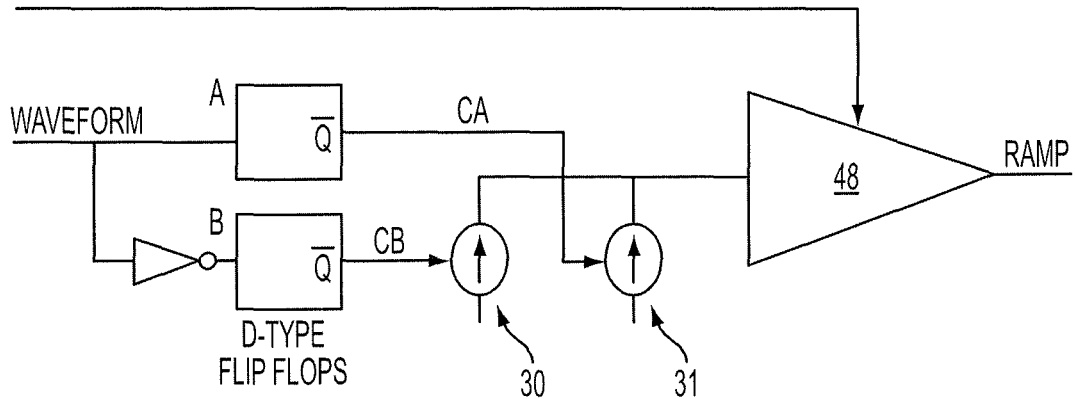
FIG. 3 shows an embodiment of an integrator circuit and waveform output of a controller for a flow sensor as shown in FIG. 2.
Figure 3B:
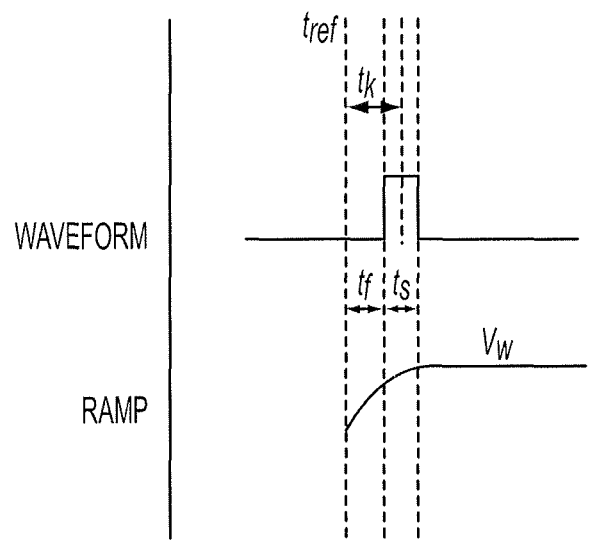

Referring to FIGS. 3a and 3b, initially, both flip-flops A and B are in the reset state causing $\overline{Q}$ to be active, thus enabling the two equal value current sources 30, 31. The integrator 48 is held inactive initially by the de-activation of the enable signal so the RAMP output is zero, At a time $t_{ref}$, the ENABLE signal is activated and the RAMP output starts to rise at a rate, which is proportional to 2 l where l is proportional to a single current source output, either 30 or 31.

After a time $t_f$ one of the WAVEFORM peaks asserts a positive edge, thus activating flip-flop A, which in turn disables one current source 31 through the control signal CA. This causes the RAMP to slow to a rate half of the previous rate.

After a time $t_s$, the WAVEFORM peak asserts a negative edge, activating flip-flop B and consequently disabling the other current source 30 through control signal CB so that no current is being fed into the integrator 48. The integrator 48 will thus hold the RAMP value at that value that was present at the fall of the WAVEFORM edge.

Thus the RAMP voltage now represents an elapsed time value from $t_{ref}$ shown as $t_k$ where:

$$t_k = t_f + \frac{t_s}{2}$$

Thus it may be readily seen that the dual slope integrator RAMP final value is proportional to the elapsed time from a reference time to the centre of the WAVEFORM pulse.

Preferably an airflow disruptor 21 is situated upstream of the flow sensor 24, to assist the flow sensor 24 in providing a more uniform determination of flow of fluid (air) within the airstream. The flow sensor 24 may be situated before the air is sampled through the detection chamber 14, or after. The flow sensor 24 may be situated in a number of different locations along the flow path of the air to be sampled. However, for best results in accurately measuring the total flow of the air drawn into the network, the preferred location is at or near the fluid inlet 20. FIG. 1 shows the flow sensor 24 located before the aspirator 16, and after a flow disruptor 21. It has been found that disrupting the flow provides a better estimate of the flow rate as ultrasonic flow detectors appear to average out the flow rate along the pipe if it is not laminar. Laminar flows may be difficult to measure consistently using an ultrasonic flow meter, as the flow profile may change.

In accordance with a preferred embodiment of the invention, when used in a smoke detector system 10 as described with reference to FIG. 1, a flow sensor 24 as disclosed herein may provide flow measurement capabilities characterized by:

providing a flow measurement function that measures the absolute volume flow rate of sample air through the air sample inlet port, namely fluid inlet 20, of the detector 10;

for inlet flow rates in the range 0 to 100 liters per minute, the detector 10 preferably has a monotonic flow measurement characteristic;

while operating over the normal environmental range, as would be familiar to the person skilled in the field of aspirated smoke detectors using sampling pipe networks, the detector 10 may achieve a maximum airflow rate measurement error of one half of the flow change obtained when any single sample hole 29 is blocked, assuming measurements are averaged over a period of 180 seconds, and;

the detector may perform its flow measurement function while in a Running state.

A more detailed description of preferred and alternate embodiments of the invention follows.

Relatively high-frequency ultrasonic transducers may be used in order to minimise interference effects from sounds generated within the smoke detector 10 or from external sources. The preferred frequency of operation is in the region 60 KHz to 90 KHz.

With reference to FIG. 6, sound pulses are sent through the air in the flow channel 26, first from transducer 42 to transducer 44 and then in the reverse direction from transducer 44 to transducer 42. The flow affects the arrival time of the pulses by retarding the first pulse and advancing the second. Accurate measurements of the transit times may be used with appropriate formulae to yield a measurement of flow.

Preferably, the transducers are positioned such that they are displaced from each other by at least 75 mm parallel to the direction of flow as indicated in FIG. 6.

Pulse Timing

In order to obtain the necessary flow resolution, it is preferable to resolve the transit time between sensors to about +/−30 nSec. For a flow channel 26 diameter of about 11 mm, and a transducer displacement parallel to the flow of 75 mm, this translates to about a 0.5 liter/minute flow error. This level of error is expected to be sufficient to meet the measurement error requirement of operating smoke detector systems. Due to noise issues it is preferable to average over the measurement period to achieve the timing required. It would be understood by the person skilled in the art that in this design utilising time-of-flight calculations, stability of measurement with time, temperature and other environmental considerations is much more important than absolute accuracy.

Flow Calibration

The nature of time-of-flight sensing is such that there is no need to calibrate the sensor or to compensate it for temperature variation. However, there may be steady state offsets in the measurement. This may require zeroing out in accordance with methods that the person skilled in the art would be acquainted with.

Data Output

It is useful to provide measurement readings in accepted standard units, For example, flow in liters per minute or speed of sound in meters per second. This may ease the task of writing interface software, which needs to interpret these values, and for users of the device who need to understand them. It is considered acceptable to provide measurements as decimal multiples of standard units to allow use of integers as the information containing data structure.

Example acceptable units are:

flow:
   liters/min
   deciliters per minute (tenths of liters/minute)

speed of sound:
   meters per second
   centimeters per second signal amplitude:
   volts
   millivolts Software Interface The following minimum set of commands from may be implemented
   1. Calibrate electronics
   2. Get Flow
   3. Get Speed of Sound
   4. Get Amplitude
   5. Get Status Detailed Design As the software, hardware and mechanicals of a preferred sensor are inter-related and to illustrate a system with both satisfactory and known characteristics, each aspect of these is now described in detail sufficient for each part to be constructed and for the algorithms to be coded in a manner as would be readily understood by the person skilled in the art.

The person skilled in the art would also appreciate that it is possible to achieve equivalent design outcomes by using different approaches. However, it should be noted that the examples given herein below are tested and are known to work, Mechanical Requirements There are some mechanical requirements, which are important in the design of an ultrasonic flow sensor.

Transducer Spacing

Figure 7A:
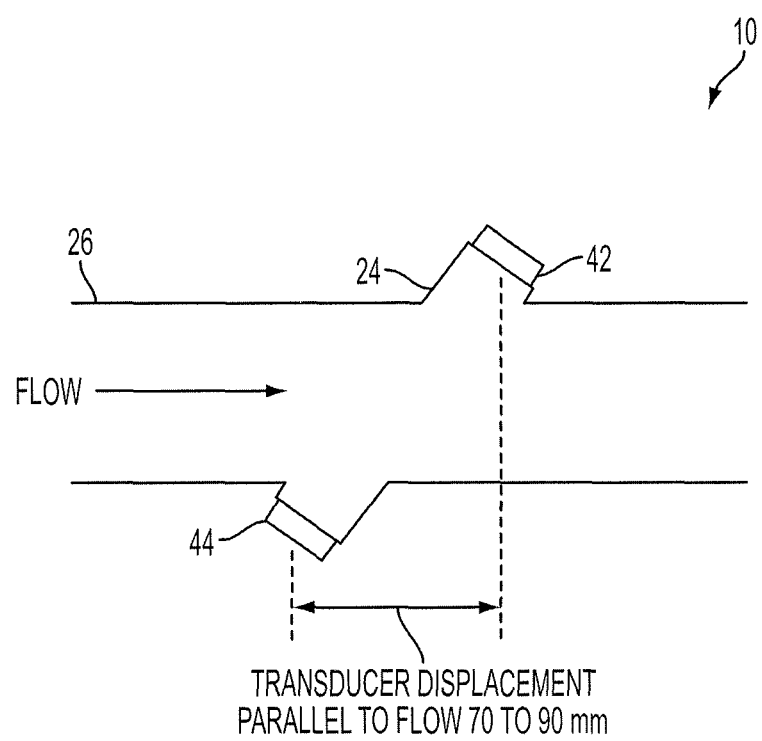
FIGS. 7a and 7b show embodiments of flow sensor transducer arrangements used for time-of-flight measurements.
Figure 7B:
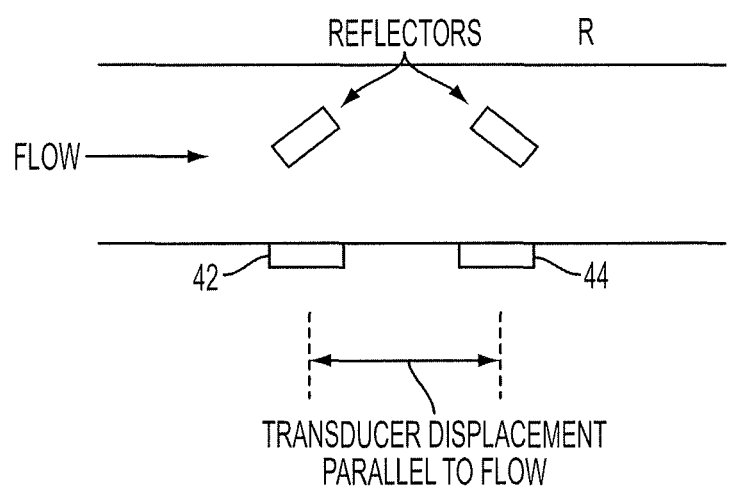
Figure 8:
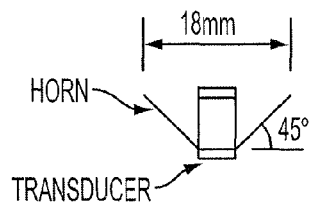
FIG. 8 shows an embodiment of a transducer reflector arrangement.

The transducers should be spaced so that they are separated along the direction parallel to the air flow by about 70 to 90 mm. If they are diagonally opposed, the distance measurement should be made along the direction of flow. The spacing perpendicular to the flow is not considered important. Examples of acceptable designs are shown in FIG. 7a and FIG. 7b. A further example of a transducer spacing arrangement, not shown, is a variant of that which is shown in FIG. 7b and comprises a single reflector for two transducers, which are positioned on the same side of the air flow. In other words, the two reflectors shown in FIG. 7b are replaced with a single reflector. The individual transducers may be cylindrical in shape and generate a cylindrical field pattern. In order to control the directionality and to improve the system gain, it is advisable to focus the ultrasonic energy. The preferred construction in this instance is to place the transducer in a horn reflector as shown in FIG. 8.

Air Path

Within the field of aspirated smoke detectors, the design of the air flow path may be considered to be constrained in two ways.

1. Firstly, it is preferable that the cross-sectional area of the air path be similar to the cross-sectional area of a standard sampling pipe (for example, a VESDA™ system with an air path cross-sectional area of about 350 mm2). This characteristic minimises flow impedance while maintaining reasonable flow velocities. If the flow section is too narrow, then the flow impedance may increase. If the flow area is too wide, the lower air flow through that section may decrease reducing the accuracy of the flow measurement.

2. The flow should preferably be turbulent. The section leading up to the flow section may therefore have some degree of step or discontinuity to ensure that laminar flow is not supported.

Proximity to Noise Sources

Although it has been found that the ultrasonic flow meter may be resistant to interference from external noise sources, it is recommended that the spacing from any transducer to the aspirator be no less than 50 mm.

Description of the Electronics

Figure 9:
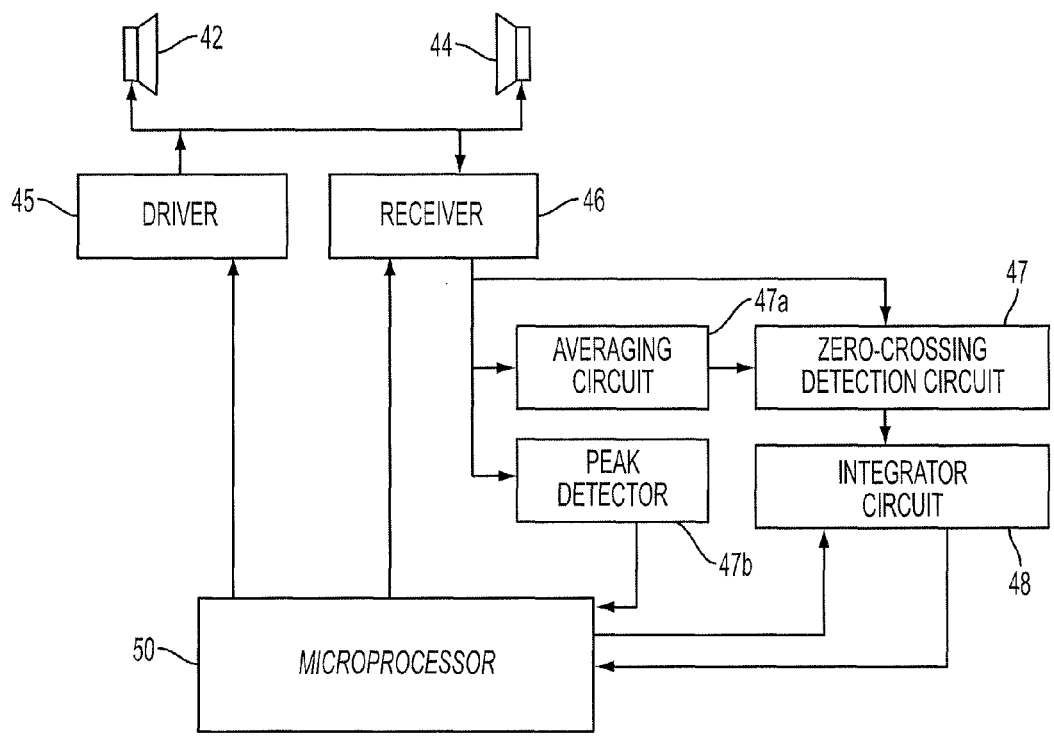
FIG. 9 shows a schematic circuit block diagram of a sensing arrangement in accordance with an embodiment of the invention.

With reference to FIG. 9 generally, and FIGS. 10 to 42, more specifically, the details of the electronic circuitry and its operations required to provide the functionality comprising the ultrasonic flow sensor is described below.

Transducers 42, 44

The transducers for use in the flow sensor design may be the US80KS-01 manufactured by Measurement Specialties Inc. The most important feature of these transducers is their relatively low Q compared with other low-cost transducers. This attribute assists the accurate determination of the timing of the received ultrasonic pulses. Accordingly, transducers with a Q of less than about 10 may be used.

Microprocessor 50 and Fuse Settings

The microprocessor 50 used in the preferred embodiment is an Atmel ATMega8. This device has 8K of ROM and 1K of RAM. It also has a multiplexed 10-bit ADC and hardware timers. The following fuse settings should be enabled to ensure correct operation.

Preserve EEPROM contents when programming
Brown out detection
High Speed Crystal Transducer Drivers 45

Figure 10:
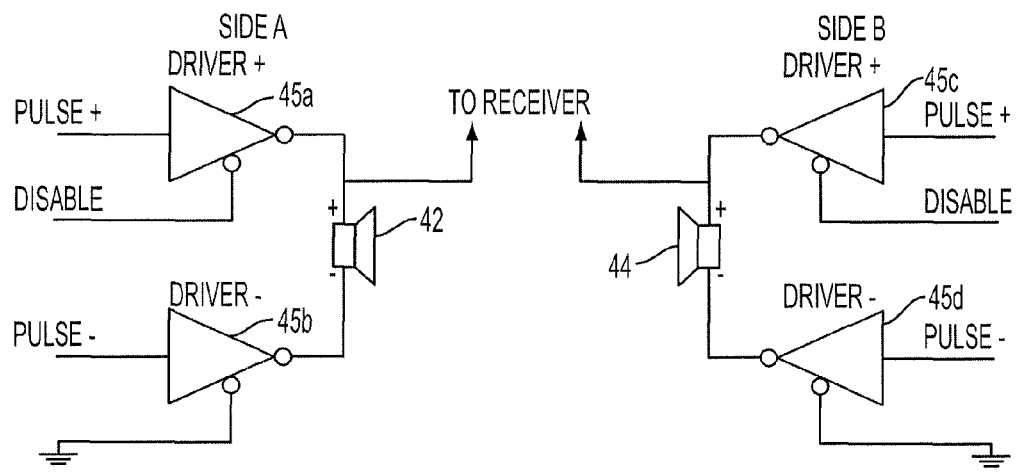
FIG. 10 shows an embodiment of a transducer driver configuration.
Figure 11:
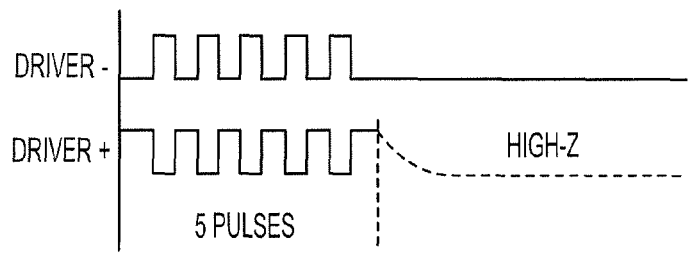
FIG. 11 shows example waveforms of driver circuits for transducers in accordance with an embodiment of the invention and illustrating a comparison of the phase of the active drive circuit arrangement waveforms.

With reference to FIG. 10, the ultrasonic transducers 42, 44 are driven by a differential 80 KHz (nominally) square wave. The drivers, 45a, 45b, 45c, 45d each provide a 15 Vpp swing and are able to be switched into a high-impedance state. The drivers are controlled by the microprocessor 50 to put out 5 pulses as shown in FIG. 11. Following the pulses, the negative side driver 45b or 45d is held low and the positive side driver 45 a or 45c is switched to high impedance.

Receive Selector

Figure 12:
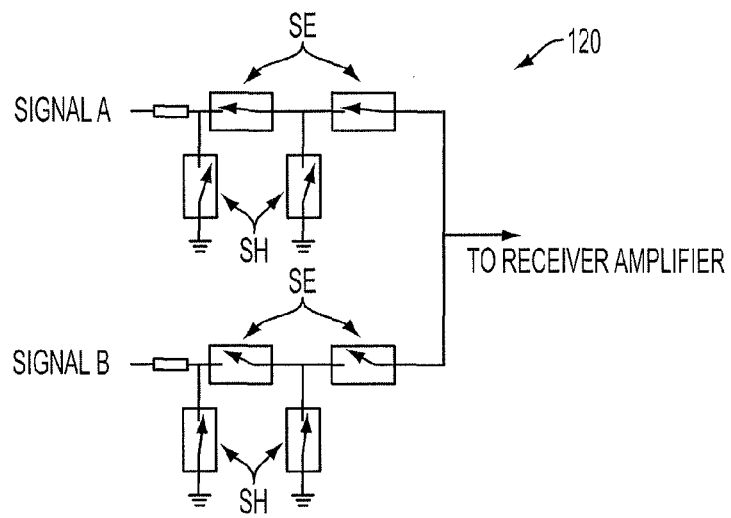
FIG. 12 is a circuit diagram showing a receiving transducer selector for selecting signal A from transducer A of two transducers A and B in a flow sensor arrangement in accordance with an embodiment of the invention.

With reference to FIG. 12, once the pulses have been generated the receive circuitry 120 is enabled. The receive circuit 120 selects (listens to) the receiving transducer 42 or 44 and deselects the sending transducer being the other of 44 or 42. Schematically, the receive selector 120 functions as follows. When it is required to receive the signal A from a transducer, the series switches SE are closed and the shunt switches SH are opened on that circuit branch. The signal B from the other transducer is not wanted and so is attenuated. This is achieved by opening the series switches for signal B and closing the shunt switches. The configuration shown is preferred as it has been found to achieve good attenuation and isolation.

Figure 13:
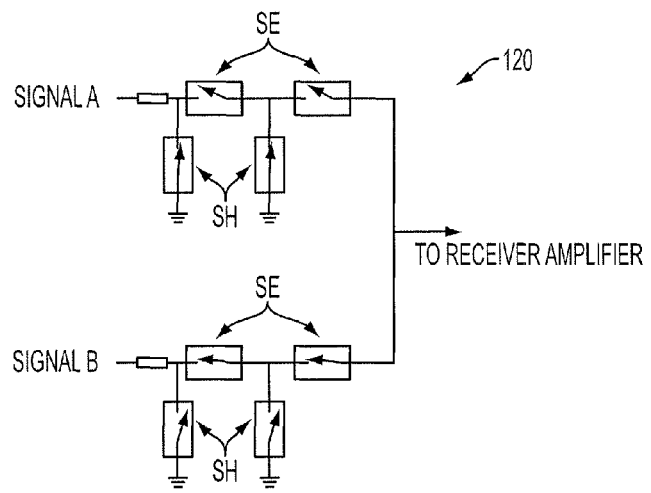
FIG. 13 is the circuit diagram of FIG. 12 showing the selector configured to select signal B from transducer B of two transducers A and B in accordance with an embodiment of the invention.

When it is required to listen to signal B from the alternate transducer, the states of all of the switches of the receiver selector 120 may be inverted with respect to the arrangement of FIG. 12, as shown in FIG. 13.

Receiver Amplifier

Figure 14:
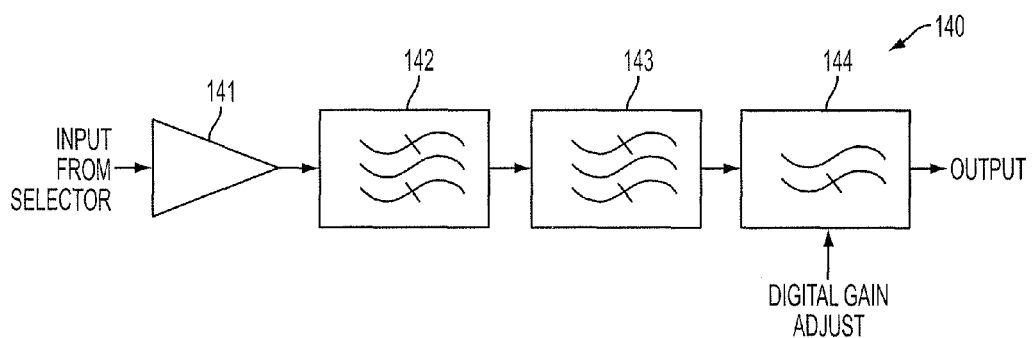
FIG. 14 is a circuit block diagram of a receiver amplifier for a flow sensor arrangement in an embodiment of the invention.

Referring to FIG. 14 a receiver amplifier 140 is shown and has a number of notable characteristics, namely:

1. Very high input impedance, >5 MOhms at the active frequency range (50 Khz to 150 KHz)
2. High gain adjustable from about 500 to 5000
3. Bandpass frequency characteristic with corner frequencies at 48 KHz and 150 KHz approximating a Butterworth characteristic with 60 dB/decade roll off at lower frequencies and 40 dB/decade at high frequencies.

The preferred implementation in this case is a multistage amplifier comprising a JFET front end 141 followed by three operational amplifier gain/filter stages 142, 143, and 144. The final stage 144 has a digitally adjustable gain setting element, which may control the gain within the range 1 to 10.

Peak Detector

In order to adjust the receiver 46 gain and to perform coarse receiver position detection, it is necessary to measure the peak value of the received signal at selectable times. A gated peak detector 47b is provided for this purpose. Its behaviour is illustrated in FIG. 15.

Figure 16:
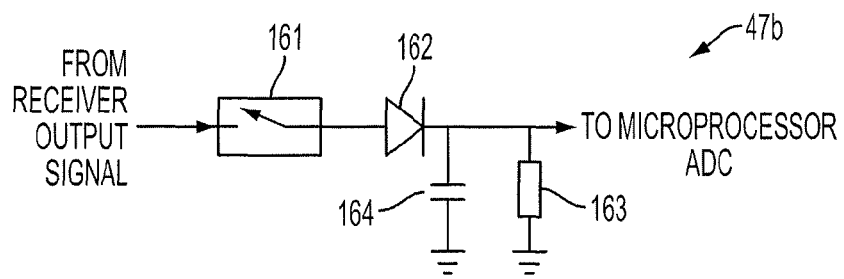
FIG. 16 is a circuit diagram of a peak detector of a flow sensor arrangement in accordance with an embodiment of the invention.

A suitable implementation for the peak detector 47b may be an analog switch 161 followed by a diode 162 and a resistor-capacitor 163, 164 network as shown in FIG. 16.

Figure 15:
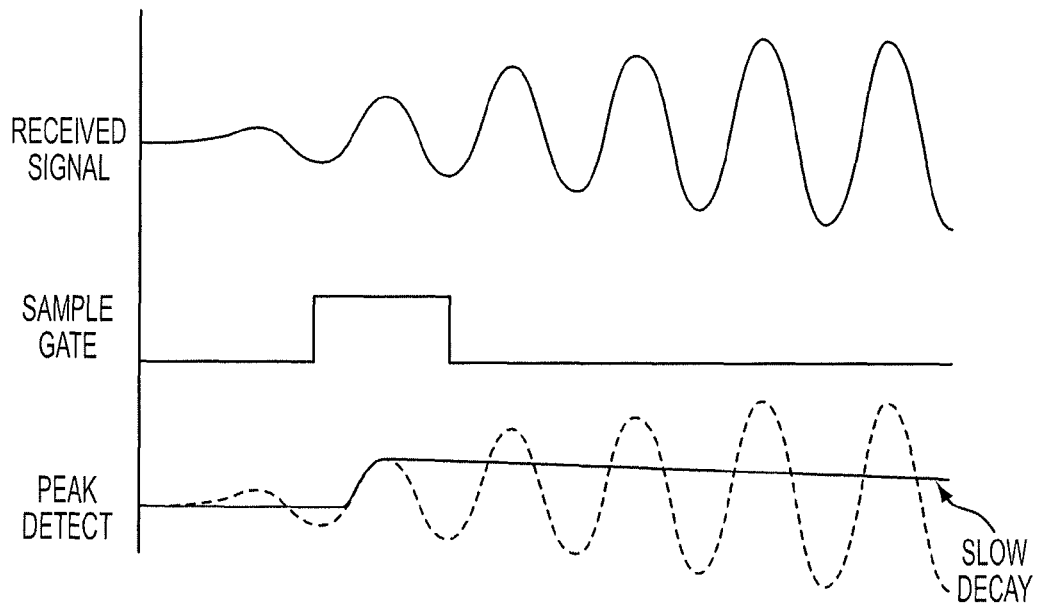
FIG. 15 shows peak detector waveforms for a peak detector of a flow sensor arrangement in accordance with an embodiment of the invention.

When the sample gate 161 is enabled, the output follows the peak of the input waveform of FIG. 15. When the gate 161 is disabled, the last sampled value decays slowly toward 0 volts. The decay time constant is about 3 mSec and the peak sampling time constant is preferably about 1 uSec.

As the peak measurements are all relative to an initial sampled value, the absolute value is not considered important. The specifications for the peak detector are:

| Parameter | Value | Tolerance |
|---|---|---|
| Sampling time constant | 1 uSec | +/−50% |
| Decay time constant | 3 mSec | +/−50% |
| Maximum output voltage | 4.4 V | +/−10% |
| Minimum output voltage | 0 V | +5/−0% |

Averager

Figure 17:
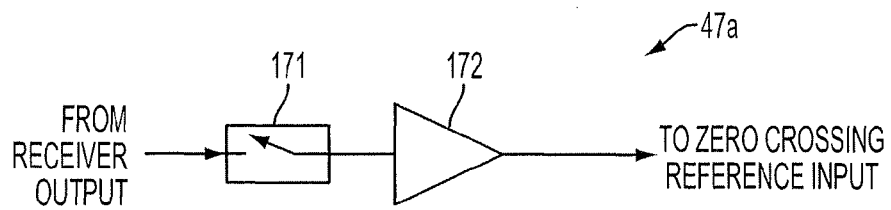
FIG. 17 is a circuit diagram of an averaging circuit for setting a zero-crossing reference level of a flow sensor arrangement in accordance with an embodiment of the invention.

An averaging circuit 47 is provided, as shown in FIG. 17 to set the reference level for a zero-crossing detection circuit, a description of which follows. The averaging circuit 47a is enabled for a sample period prior to the arrival of the received ultrasonic pulse train, The circuit averages out signal noise at this time and samples the background signal DC level. When the averaging circuit sample gate 171 is disabled, the circuit retains this average background value as a reference to feed into the zero crossing detector. The preferred specifications for the averager 47a are:

| Parameter | Value | Tolerance |
| --- | --- | --- |
| Rise time | 200 uSec | +/−10% |
| Damping factor | 0.7 | +/−10% |
| Decay Time Constant | 0.05 sec | Minimum |
| Maximum output voltage | Vcc | +0/−5% |
| Minimum output voltage | 0 V | +5/−0% |

Figure 18:
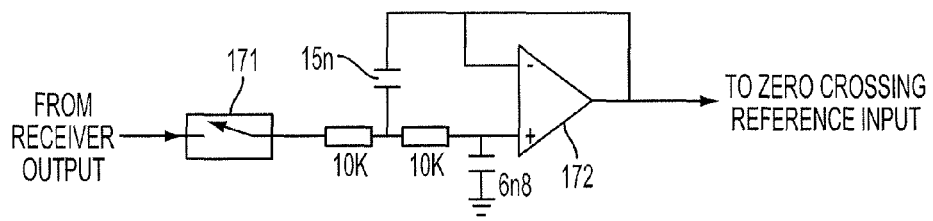
FIG. 18 is a circuit diagram of the averaging circuit of FIG. 17 in more detail showing a low-pass filter circuit arrangement.

The averager may be implemented as low pass filter 172. Referring to FIG. 18, the low-pass filter 172 is preferably an active filter with a parallel capacitive component at the input, which is required to hold the stored average value when the gate 171 is disabled.

Zero-Crossing Detection Circuit 47c

Figure 19:
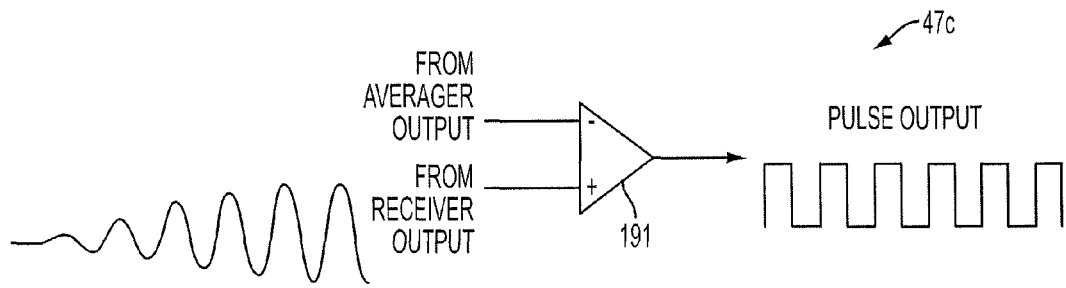
FIG. 19 is an illustration of waveforms of a zero-crossing detector circuit of a flow sensor arrangement in accordance with an embodiment of the invention.

Referring to FIG. 19 a zero-crossing detection circuit 47c is included to provide an output indicating the presence and polarity of zero crossings in the received signal. This functionality may be provided with a simple, high-speed voltage comparator 191. The comparator 191 output is high when the receiver signal is higher than the average level and low when the receiver signal is lower than the average level. Each pulse edge corresponds to a zero crossing transition of the received signal. The preferred specifications for the zero-crossing detection circuit 47c are:

| Parameter | Value | Tolerance |
| --- | --- | --- |
| Output rise time | 100 nSec | Max |
| Propagation delay | 50 nSec | Max |
| Output voltage range | HCMOS compatible | |
| Input voltage range | 0 to 5 V | Nominal |
| Input hysteresis | 10 mV | Minimum |

Pulse Position Detector Circuit

The pulses from the zero-crossing detector circuit 47c correspond to peaks in the received signal. In order to accurately determine the transit time of the pulse from transmission to reception, it is necessary to accurately locate a signal artefact such as a peak or a series of zero crossings etc. It is noted that a single zero crossing may not be acceptable as a timing feature because its position jitters with small changes in offset. Similarly a threshold arrangement may be considered unacceptable as its position depends on signal amplitude.

It is possible to estimate the position of a peak by measuring the times of the zero crossings on either side of it and averaging them. This is a robust approach to peak location as offsets in the signal due to low-frequency interference or noise are cancelled out.

Figure 20:
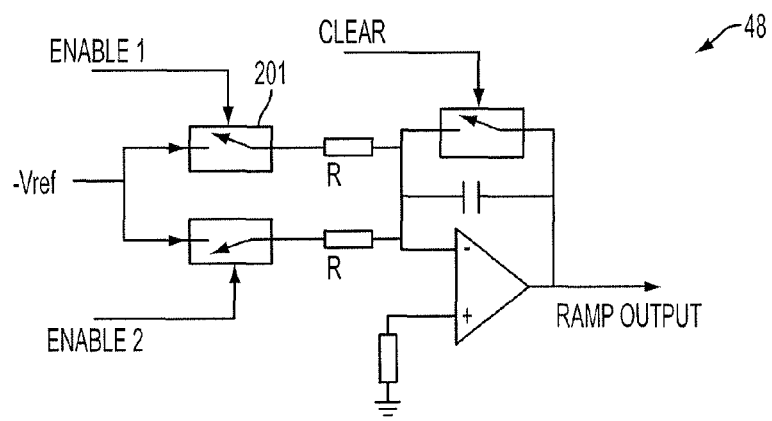
FIG. 20 shows a circuit diagram of an integrator circuit used in a pulse position detector of a flow sensor arrangement in accordance with an embodiment of the invention.

A circuit suited to the task of locating the zero crossings and averaging them is the Dual Slope Integrator 48. FIG. 20 shows a preferred circuit structure of the dual slope integrator 48.

Figure 21:
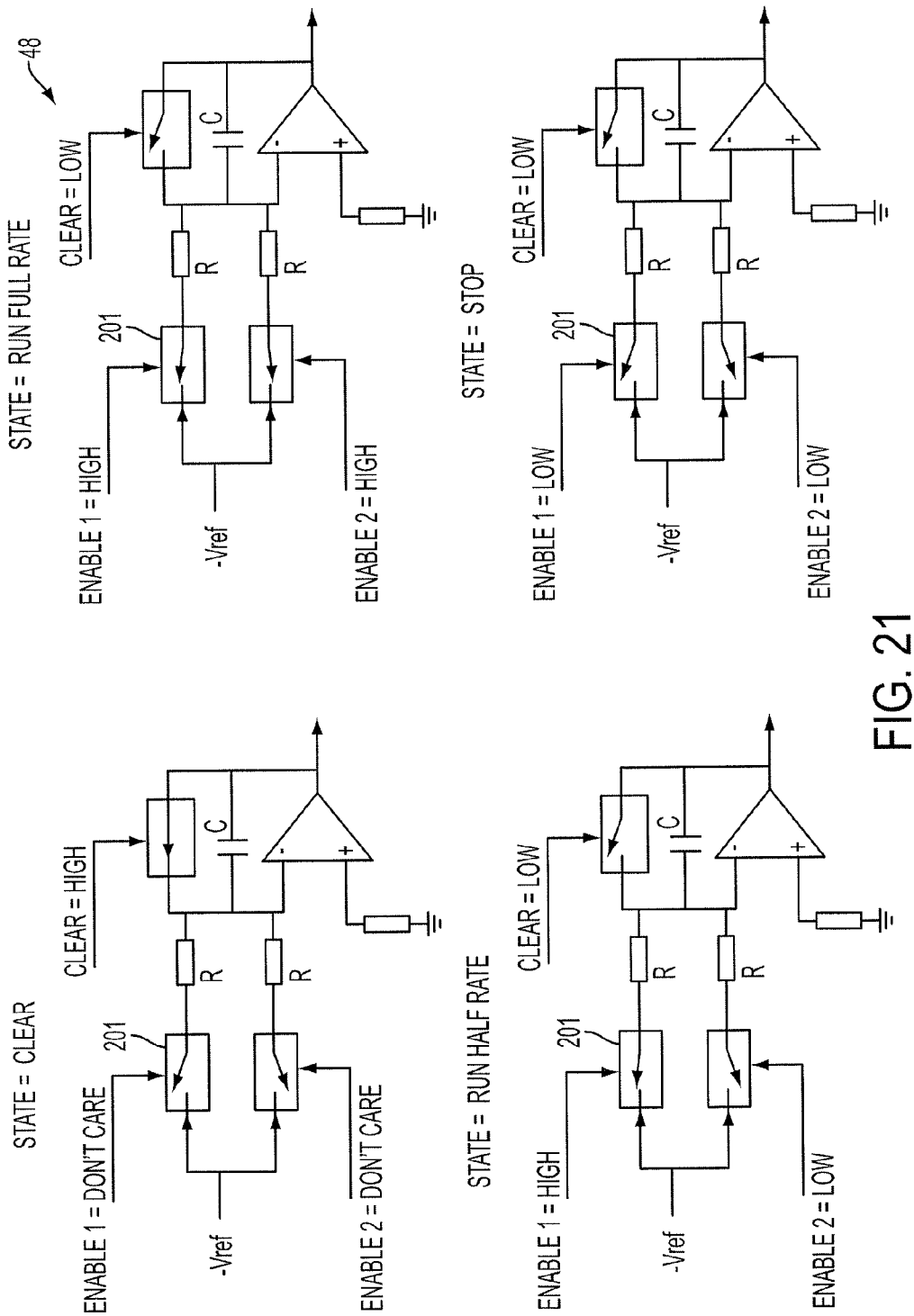
FIG. 21 shows four operating states of the integrator circuit of FIG. 20.
Figure 22:
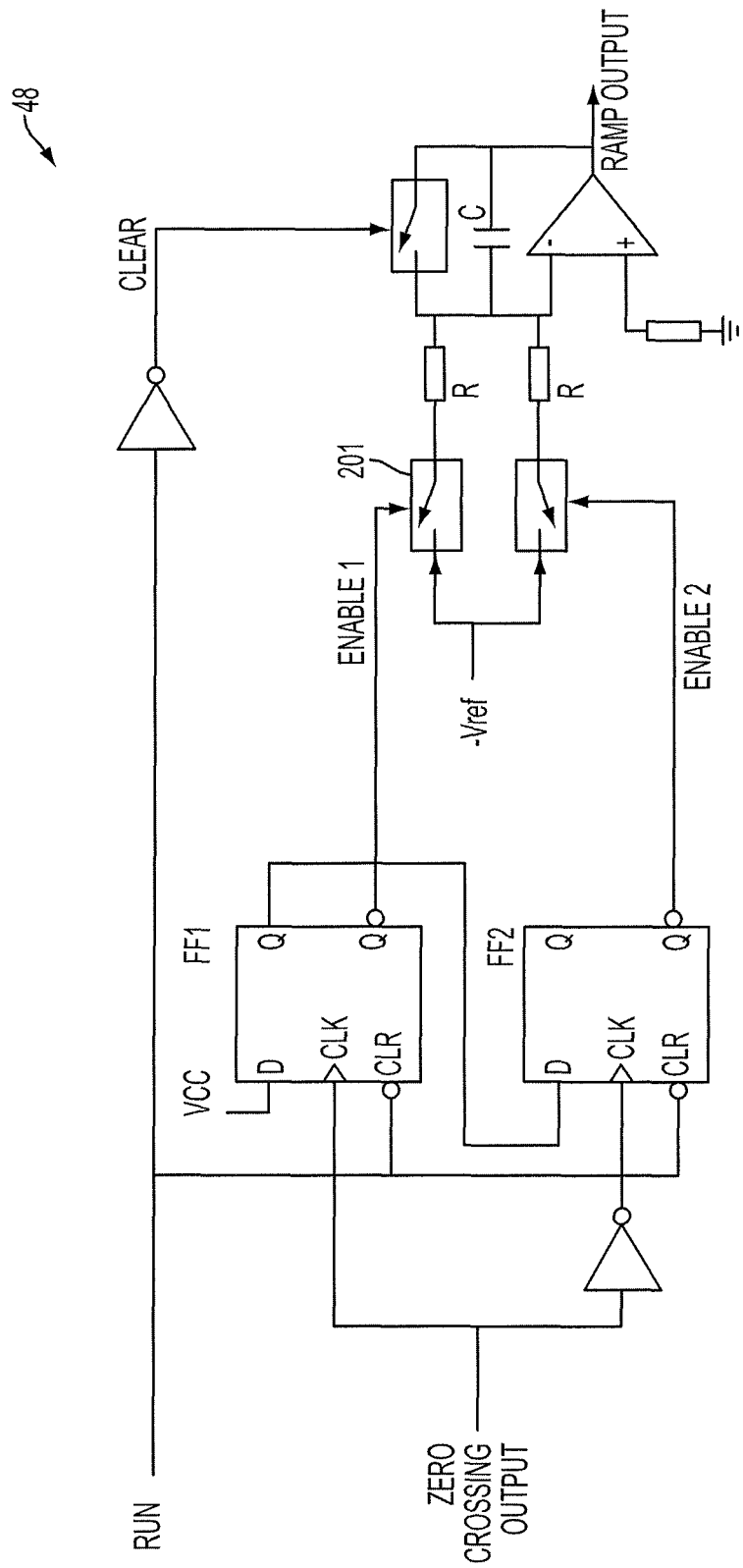
FIG. 22 shows a circuit diagram of the integrator circuit of FIG. 20 with an exemplary control circuit.
Figure 23:
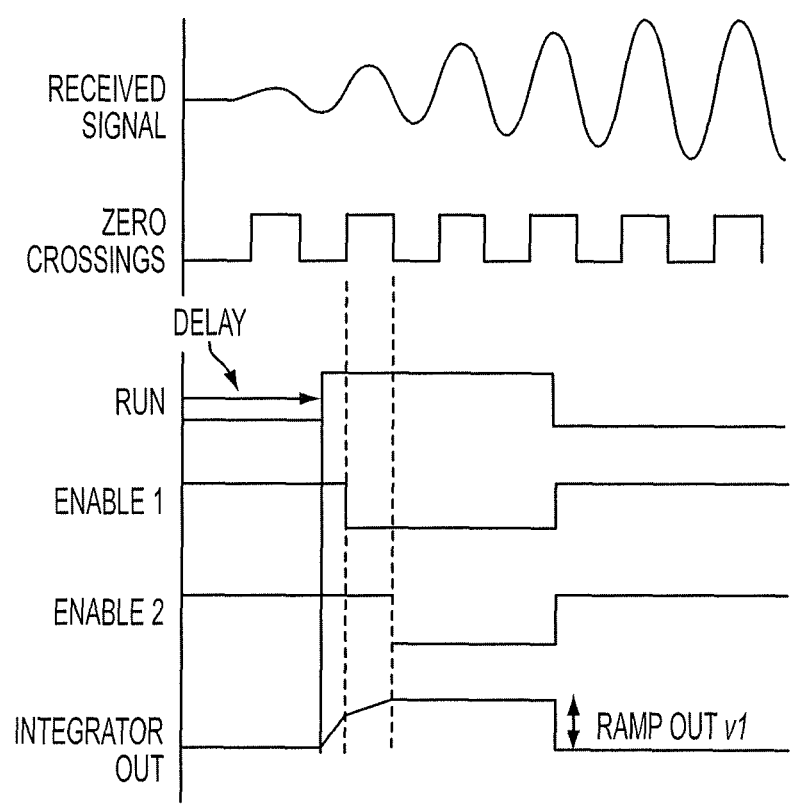
FIG. 23 shows waveforms of the integrator circuit of FIG. 20.

Referring to FIG. 21 in more detail, there are four modes of operation of the dual slope integrator or ramp circuit 48. They are Clear, Run full-rate, Run half-rate and Stop. The switch positions for each of these states is shown in FIG. 21. The states may be controlled by two flip-flops and two inverters. The overall circuit is shown in FIG. 22. Sample waveforms for the ramp circuit 48 are shown in FIG. 23 and correspond in more detail to those shown in FIG. 3b. At a predetermined time, the system microcontroller 50 enables the RUN signal. RUN is indicated in FIGS. 20, 21 and its waveform is shown in FIG. 23. The enabling of the RUN signal opens the switch 201 across the integrating capacitor C allowing it to charge up at a particular rate, R. At the occurrence of the next positive edge of the zero crossing waveform, the ENABLE 1 signal turns off, dropping the charge rate to R/2. The falling edge of the zero crossing signal turns off the ENABLE 2 signal causing the integrator to stop charging and to hold its value. This value may be read by the ADC of the microcontroller 50. Once the value has been read, the microcontroller 50 drops the RUN signal, clearing the integrator 48 and resetting the flip-flops, FF1 and FF2 of FIG. 22, to their initial state. Thus, this circuit locates the position of the peak in question, relative to the RUN edge, by averaging the times of the +ve and −ve zero crossings of the received signal. The value of the integrator output is directly proportional to time from the rising edge of the RUN signal to the centre of the peak that follows that edge. The preferred specifications for the ramp circuit 48 to detect pulse position are:

| Parameter | Value | Tolerance |
| --- | --- | --- |
| Input Logic Levels | HCMOS Compatible | |
| Fast Ramp Slew Rate | 0.26 V/uSec | +/−20% |
| Slow Ramp Slew Rate | 0.13 V/uSec | +/−20% |

Software Implementation

Figure 24:
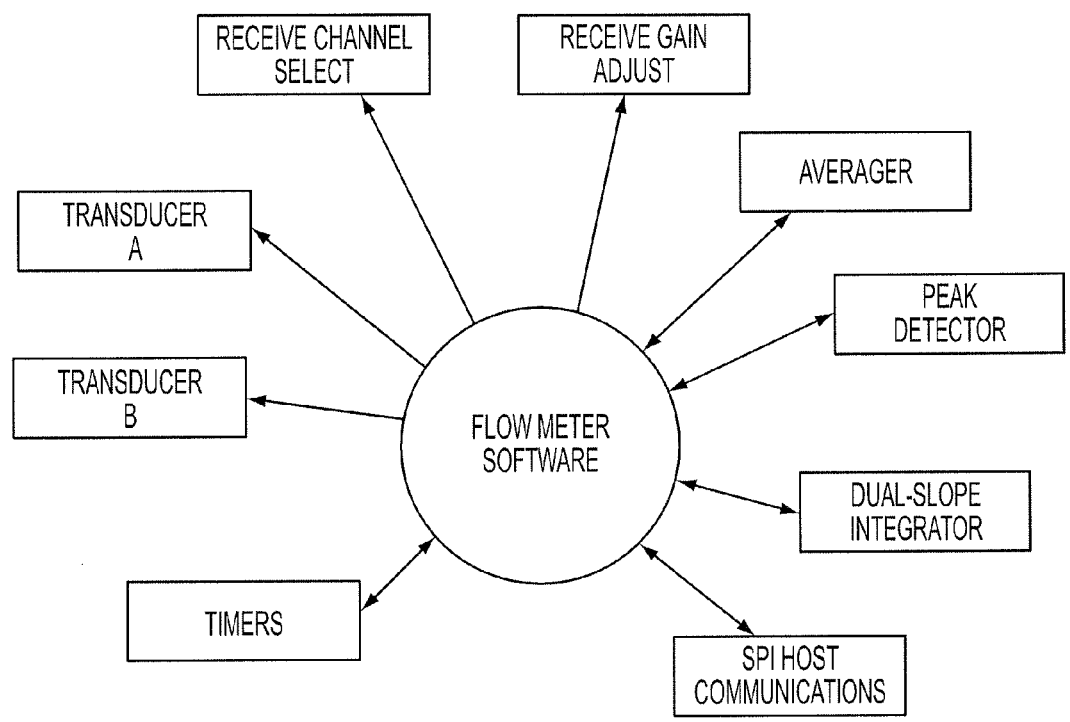
FIG. 24 shows a software context diagram of a flow sensor arrangement in accordance with an embodiment of the invention.

The method of operating the ramp circuit 48 is described below with respect to an exemplary software implementation of an improved smoke detector system 10. The following describes the detail of how to perform fundamental operations required of the software. A Software Context Diagram relating to the operation of a preferred embodiment of the invention is illustrated in FIG. 24.

Software Method Requirements

There are a number of functions which the software performs in order to operate the flow sensor reliably, as follows:
1. Adjust gain
2. Determine transducers' resonance frequency
3. Search for received pulses
4. Track changes in the wavefront position
5. Calibrate electronics to account for component variations
6. Store and retrieve parameters in non-volatile storage
7. Communicate with a host
8. Accurately time the arrival of the received signal in each of two directions Software Structure The software developed for the Flow Sensor has the following advantageous features:
1. There is no operating system or background task handler.
2. All individual functions are slaved to external events.
3. The only interrupts used are for communications with the host system.
4. All interrupts are disabled during critical timing measurements.

Overall Operation

Figure 25:
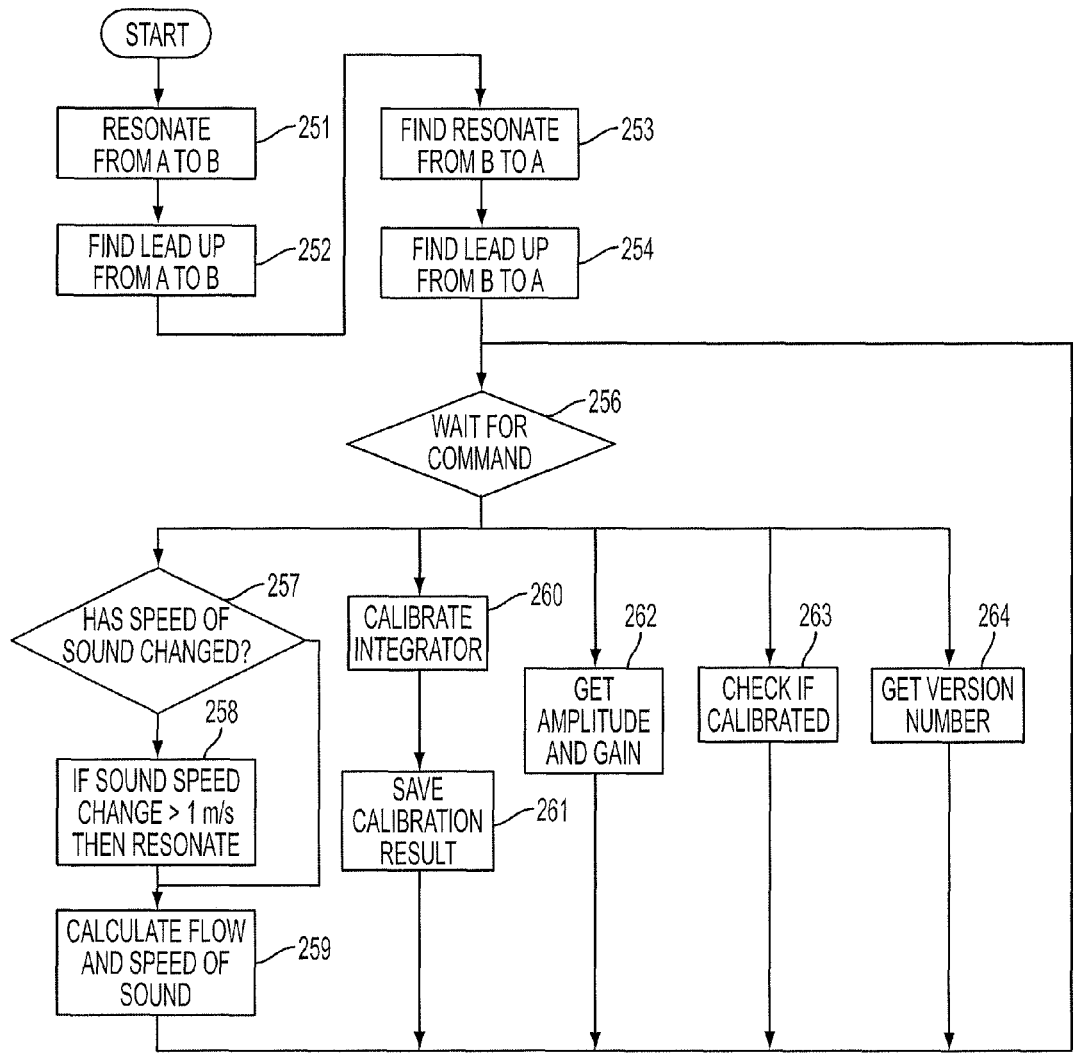
FIG. 25 is a flow chart of an overall program used in the operation of a flow sensing arrangement in accordance with an embodiment of the invention.

The overall operation of the flow sensor 24 is described by the flowchart of FIG. 25.

In the flow chart of FIG. 25, the program starts by determining the resonance from transducer A to transducer B at step 251. That is, the observed resonance when transmitting from transducer A and receiving with transducer B. This resonance determination step is required in this embodiment as other routines do not work correctly unless the transducers are driven at their resonant frequency.

The next step, FindLeadUp 252, is to determine the approximate time taken for the transit of a pulse from A to B. This arrival time may be determined to within one quarter of a cycle of the transmitting waveform. This step finds the time of flight by determining the location of the aforementioned point of diversion. Other routines may refine this estimate in order to get an accurate measure of the transit time.

At steps 253 and 254 Resonate and FindLeadUp are then called respectively for the reverse direction, i.e. transmitting from transducer B and receiving at transducer A. At this point the flow sensor 24 is ready to process a command from the host and waits for a command at step 256. A preferred set of commands with reference to FIG. 25 are:

| Command | Description | Comment |
|---|---|---|
| GET_FLOW<br>Steps 257, 258 and 259 | Start a flow measurement and return the result | Returns Flow in 100 x l/m and Speed of Sound in 10 x m/sec |
| SET_ZERO_CAL<br>Steps 260 and 261 | Calibrates the Electronics, flow zero value and saves the measured speed of sound | This should be done at between 20 C. and 30 C. |
| GET_AMPLITUDE<br>Step 262 | Requests last measured signal amplitude and amplifier gain setting | Returns amplitude 512 (approx min) to 1023 (max) and gain setting 1 to 100 |
| IS_CALIBRATED<br>Step 263 | Request calibration status | Returns a status flag indicating whether or not the sensor has been calibrated using the SET_ZERO_CAL command. |
| GET_VERSION<br>Step 264 | Requests firmware version number | |

If a GET_FLOW command is received while in wait at step 256, the program first calculates flow and speed of sound using the routine CalcFlowAndSound( ) at branch steps 257, 258 and 259. This routine measures the transit time of the ultrasound pulse in each direction (from A to B and from B to A) while at the same time, tracking the position of the wave to ensure that it doesn't move out of range. The resultant flow measurement and speed-of-sound measurements are available to send to the host. The program may check to see if the speed of sound has changed significantly from the value calculated in the preceding call, steps 257 and 258. If there has been a significant change in the speed of sound then the Resonate( ) routine is called at step 258 to maintain system tuning.

If a "calibrate electronics" command is received while in wait step 256, the unit performs a routine to calibrate the receiver electronics against component variation at branch steps 260 and 261. This is NOT a flow calibration but simply an internal self calibration. Preferably, this operation should be done under zero-flow conditions; and the inlet pipe 26 should be blocked. This routine also records the measured speed of sound as a reference, step 261.

If the received command while in wait step 256 is to retrieve amplitude, then the amplitude of the received ultrasonic pulse and the gain setting of the receive amplifier are sent to the host at step 262. This command is a good "health" indicator of the detector as a low amplitude reading is indicative of either strong contamination or device failure.

Sending Pulses

Figure 26:
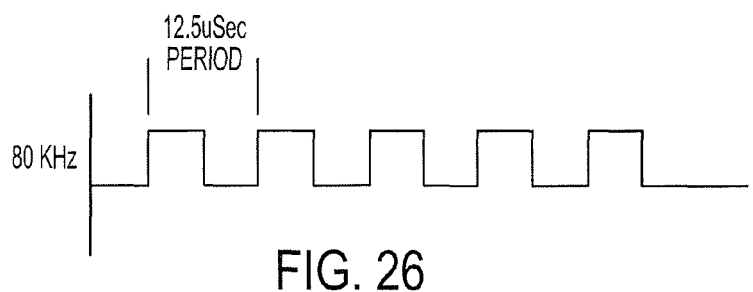
FIG. 26 shows an exemplary pulse train of an ultrasonic transmitter in accordance with an embodiment of the invention.

In order to measure flow, the microcontroller 50 is required to first send a sequence of ultrasonic pulses, ordinarily in the form of a pulse train. Other waveforms, such as a burst of sine or triangular waves are also acceptable. In the preferred implementation, the controller sends 5 pulses with a period of 12.5 uSec and 50% duty cycle as illustrated in FIG. 26.

Wait Routines

The wait routines in the preferred implementation are based on hardware timers. Software optimisation is set for maximum speed so that the overhead associated with timing activities is minimised.

Burst Pattern Description

Figure 27A:
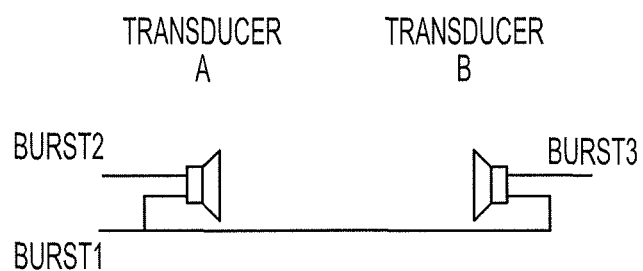
FIG. 27 shows exemplary waveforms for driving transducers of a flow sensor arrangement in accordance with an embodiment of the invention.
Figure 27B:
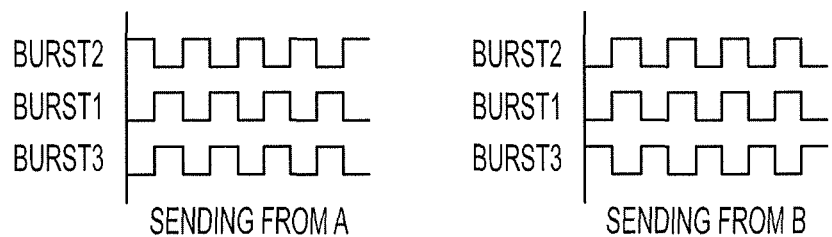

When the transducers 42, 44 are driven, one transducer (the active one) is driven by an antiphase drive signal, producing maximum acoustic output. The non-driven transducer is driven by an in-phase drive signal so that the potential difference across it is zero and it therefore it produces no output. The transducer arrangement and the corresponding resultant waveforms are shown by example in FIG. 27*a* and FIG. 27*b*, respectively. It can be seen by inspection of the example of FIG. 27*b* showing a "sending from A," that when it is desired to send from transducer A, the drive signals to it, viz. burst1 and burst2, are anti-phase. This is in contrast with the drive signals to transducer B, also shown in the example of FIG. 27*b*. In the second example, 'sending from B' the reverse condition exists. In this instance, burst2 is now in phase with burst1 and, burst3 is antiphase with respect to burst1. Since the waveforms are generated by setting bits on an output port, the following patterns may be cycled to produce the conditions noted above.

Sending from Transducer A

| | $1^{st}$ half cycle | $2^{nd}$ half cycle |
|---|---|---|
| burst2 | 1 | 0 |
| burst1 | 0 | 1 |
| burst3 | 0 | 1 |

Sending from Transducer B

| | $1^{st}$ half cycle | $2^{nd}$ half cycle |
|---|---|---|
| burst2 | 0 | 1 |
| burst1 | 0 | 1 |
| burst3 | 1 | 0 |

Sampling the Received Waveform

Figure 28:
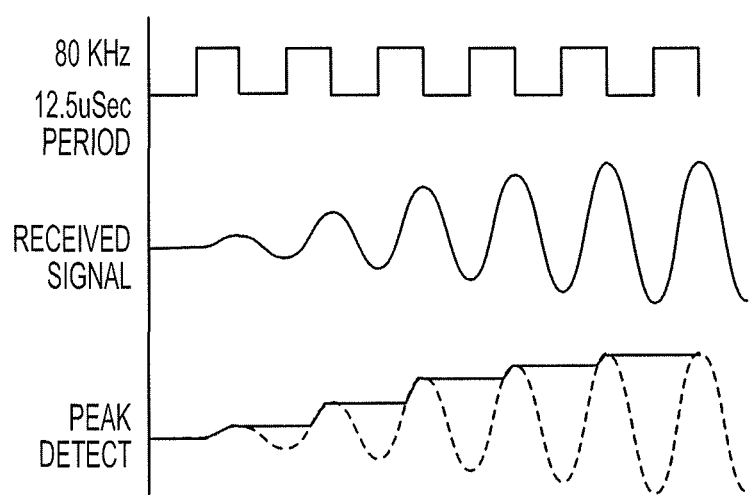
FIG. 28 shows waveforms appearing at a receiving transducer and peak detector of a flow sensor arrangement in accordance with an embodiment of the invention.
Figure 29:
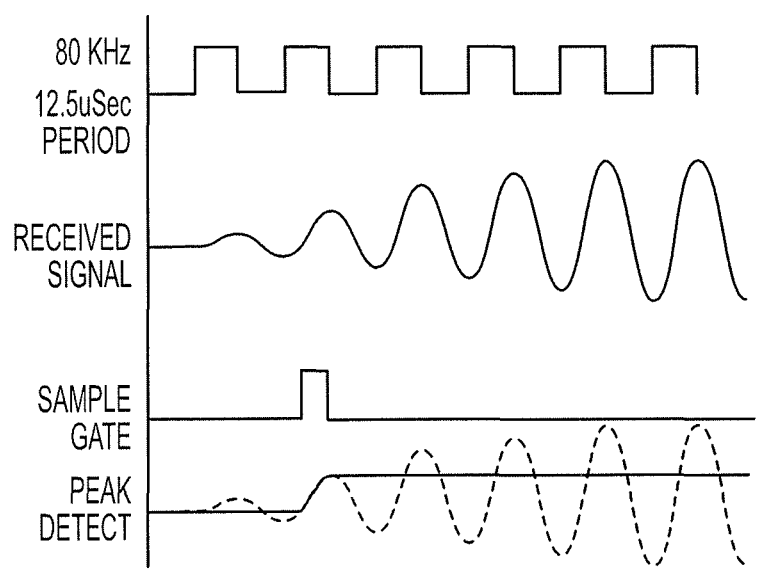
FIG. 29 shows exemplary waveforms for a gated peak detector of a flow sensor arrangement in accordance with an embodiment of the invention.
Figure 30:
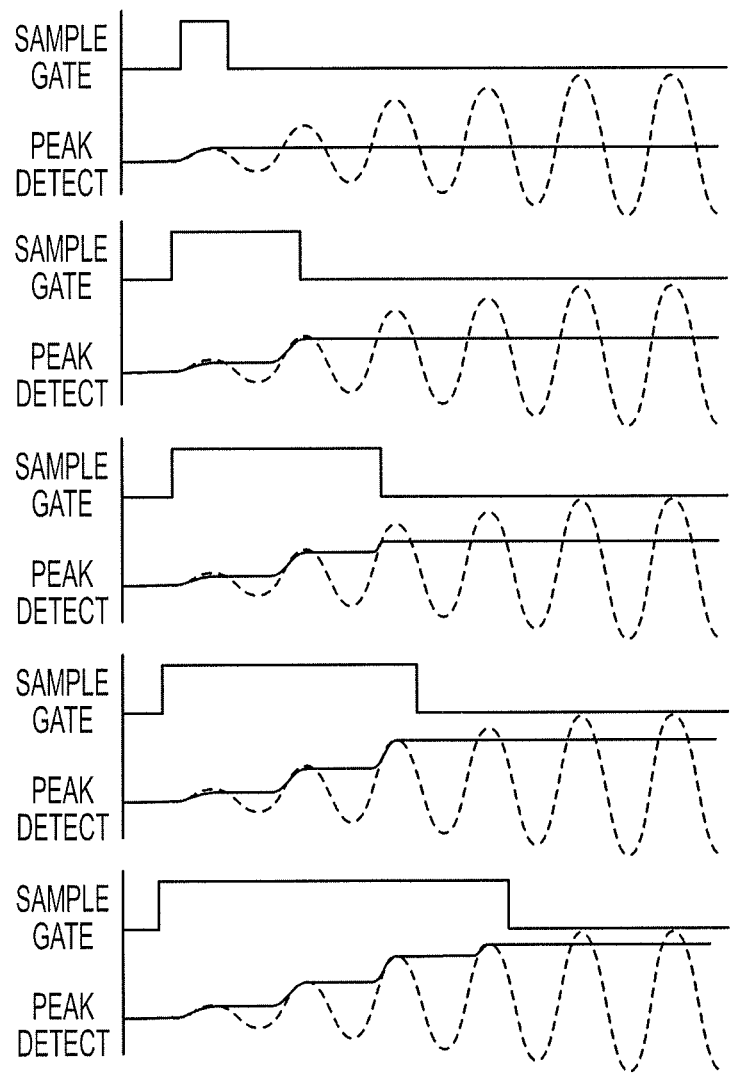
FIG. 30 shows a series of waveforms over a time interval illustrating the expansion of a peak detector's sample time in accordance with an embodiment of the invention.

A number of routines require the sampling of the received waveform at various time points. Routines such as Auto-Gain( ), step 262 of FIG. 25, and FindLeadUp( ) steps 252 and 254 of FIG. 25, are examples. The ADC on the Atmel ATMega8 (microprocessor 50) has a sample-and-hold circuit with a short, fixed sample time. This is therefore modified to provide a separate sample-and-hold which has a sample gate controlled by the microprocessor 50 allowing the software to sample over long or short periods as required. When used with long sampling times, the circuit acts as a peak detector, following the "highs" of the received signal as shown in FIG. 28. This peak-detector mode is useful in the AutoGain routine of step 262 in FIG. 25, in order to establish the peak amplitude of the received signal. Other routines require sampling of the waveform for short periods of time. The FindLeadUp( ) (steps 252 and 254, FIG. 25) routine samples the waveform for 2 microseconds at successive time points in order to measure the instantaneous voltage at that time. This cannot be done with just one burst as the microprocessor ADC is too slow. Since the signal is repetitive, sampling and holding the signal at a particular time after a burst allows the microprocessor 50 to record the reading at the sample time. Sliding the sample window allows the microprocessor 50 to scan over the received signal and plot out the envelope over successive bursts, as shown in FIG. 29. So with a sample gate time of about 1 to 2 microseconds, it is possible to get a reasonable indication of the peak value during that time. It can be seen that by iteratively expanding the sampling gate, the final value of the peak detect circuit 47b may be made to follow the peak value of the underlying waveform and hold that value when the gate, 161 of FIG. 16, is disabled, as shown in the successive waveform diagrams of FIG. 30.

Set Gain—AutoGain( )

Figure 31:
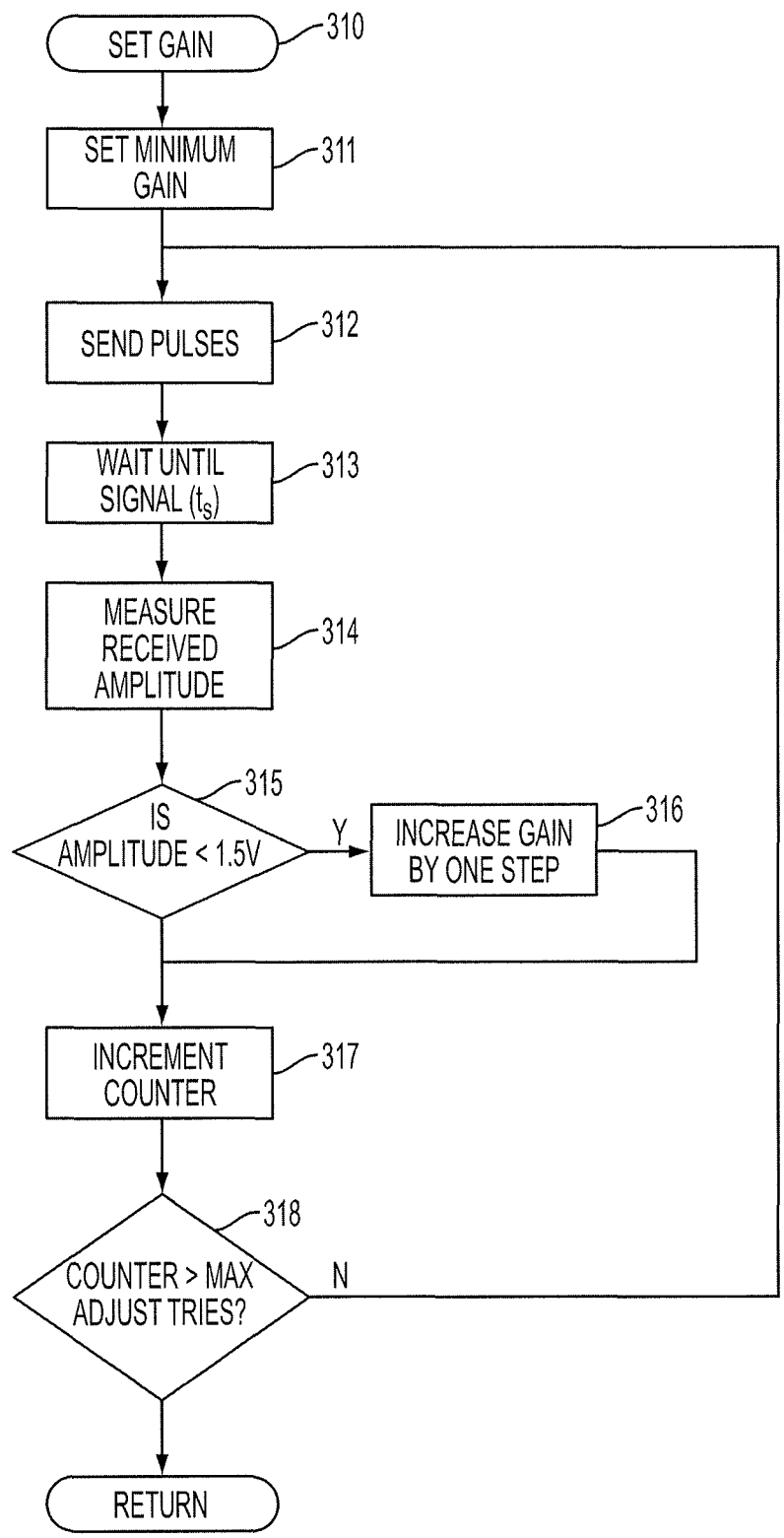
FIG. 31 shows a flow chart of a program used for gain setting in accordance with an embodiment of the invention.
Figure 32:
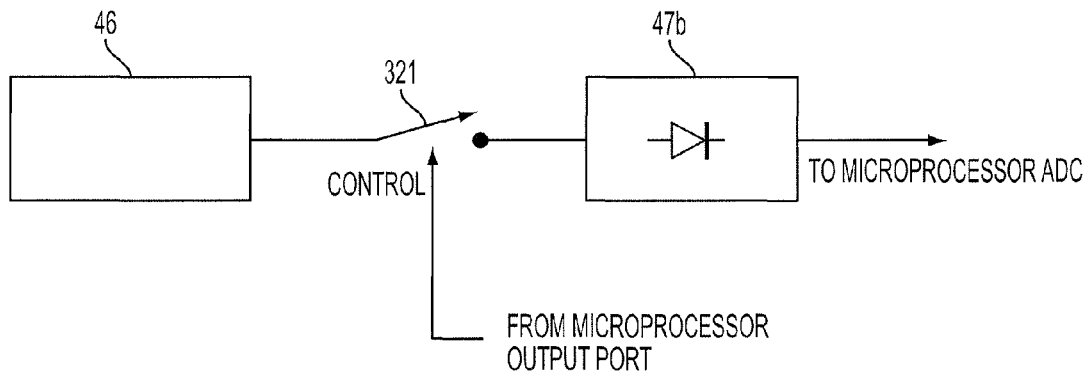
FIG. 32 shows a block diagram of a peak detector and sample gate in accordance with an embodiment of the invention.

This routine is designed to set the gain of the receive circuit, either through transducer 42 or 44, so that the received signal amplitude is about 70% of full scale. The reason that it is undesirable to have more amplitude than this is that out-of-band signals may cause saturation of the receive circuit resulting in loss of timing information. The corresponding program flow of the Gain setting routine 310 is illustrated in the flowchart of FIG. 31. A minimum gain is set at step 311. Pulses are sent by the transmitter at step 312. The software samples the peak signal over the time interval of 410 uSec to 480 uSec at steps 313 and 314 of FIG. 31. This sampling is regardless of temperature and air flow. Signals are measured using a sample gate 321 which connects the receiver 46 output to a peak detector circuit 47b as shown in FIG. 32.

The peak detector circuit 47b tracks the peak amplitude of the signal when the sample gate 321 is enabled. The peak detector 47b holds the sampled value when the sample gate 321 is disabled, allowing time for the microprocessor ADC to measure the value.

At step 315 of FIG. 31, if the measured amplitude is less than the required set point, the gain is incremented at step 316.

With regard to numerical values determined at steps 317 and 318, the peak detector 47b may, at most, produce a voltage of 5-0.6=4.4V. This translates to an A/D output value of about 900 counts. The minimum possible amplitude is the zero-signal quiescent voltage of the last amplifier which is about 2.5V-0.6V or about 1.9V. This is equivalent to an A/D count of about 390. The maximum number of iterations is 100 (the adjusting potentiometer "wiper" has either 32 positions or 100 positions depending on which type is fitted to the circuit board).

Note that an alternate embodiment of this aspect of the invention is the use of variable duty cycle of the transmitted waveform to affect gain change. Maximum energy is imparted to the transducers when they are driven with a waveform with a 50% duty cycle. Gain reduction may be achieved if required by manipulating the duty cycle of the transmitter waveform.

Finding Transducer Resonance

The resonant frequency of the transducers 42, 44 may vary considerably from about 60 KHz to 92 Khz depending on the batch and temperature of operation. It is important to drive the transducers at their resonant frequency for two reasons.

1. Maximum signal coupling is obtained at resonance
2. Signal phase shift is 0 degrees at resonance, which is important for timing considerations.

Figure 33:
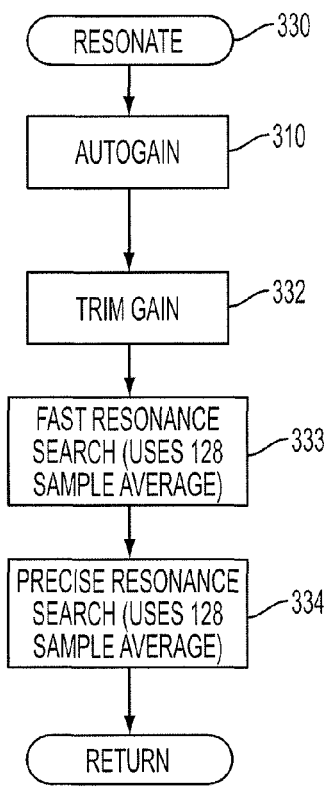
FIG. 33 shows a flow chart of a transducer resonance seeking program in precise mode in accordance with an embodiment of the invention.
Figure 34:
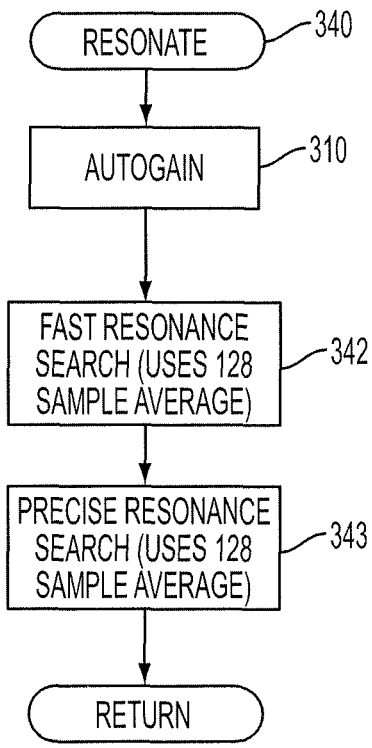
FIG. 34 shows a flow chart of a transducer resonance seeking program in course mode in accordance with an embodiment of the invention.

The resonance is found by changing the drive frequency to the transducers 42, 44 and measuring the amplitude of the received signal. The frequency which achieves the highest amplitude is the resonant frequency. The resonance seeking routine Resonate( ) 330, 340 may run in a precise mode (mode=0) designated as routine 330 as shown in FIG. 33 and coarse mode (mode=1) designated as routine 340 as shown in FIG. 34. In precise mode as shown in FIG. 33, the AutoGain routine is run at step 310. At step 332 the gain is trimmed by a course sweep performed over frequencies and the gain is adjusted down if the amplifier 140 nears saturation. A fast frequency sweep is performed at step 333 and the frequency Fc at which the largest received signal is obtained is stored. At step 334 a more precise search is performed where the drive frequency is varied around Fc in small increments and a determination is made of the frequency $F_p$ corresponding to the largest received signal. In course mode as shown in FIG. 34, the AutoGain routine is again run at step 310. However, the trim gain step 332 of the precise mode routine 330 is omitted by routine 340. Thereafter the course mode routine follows the same steps as the precise mode at steps 342 and 343.

Gain Iteration While Finding Resonance

In the course of finding the transducers' resonance, the first thing the firmware does is to select a default drive frequency and then adjust the system gain to get an acceptable received amplitude. If the transducers' resonant frequency is well away from this initial drive frequency then as the firmware searches for resonance, the receive circuit is likely to saturate because the coupling efficiency will improve dramatically as resonance is approached. Saturation of the received signal means that it is not possible to discriminate the resonant peak. The firmware overcomes this problem by adjusting the gain up and down as required in an iterative fashion while sweeping the drive frequency to ensure that resonance is found without causing amplifier saturation. Once the optimum gain has been set, a fine frequency adjustment is undertaken to accurately determine the resonance frequency.

Finding Received Pulse Train—FindLeadUp( )

A routine is required to locate the arriving pulse train waveform. A simple threshold method is not desirable as this may be susceptible to being unstable or unreliable, for example, it may tend to be affected by minor changes in amplitude. The following description identifies the approach taken by the present invention according to a preferred embodiment.

Locating the Measurement Peak

Figure 35:
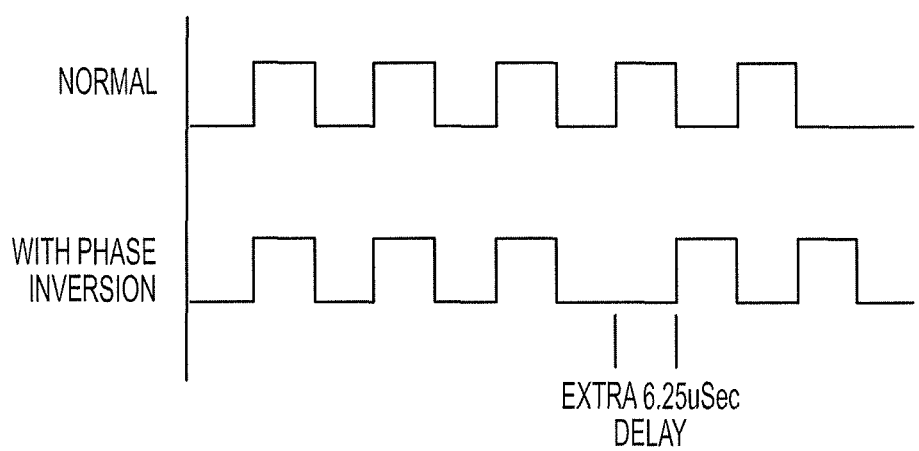
FIG. 35 shows a transmitter ultrasonic signal pulse train with an introduced phase inversion in accordance with an embodiment of the invention.
Figure 36:
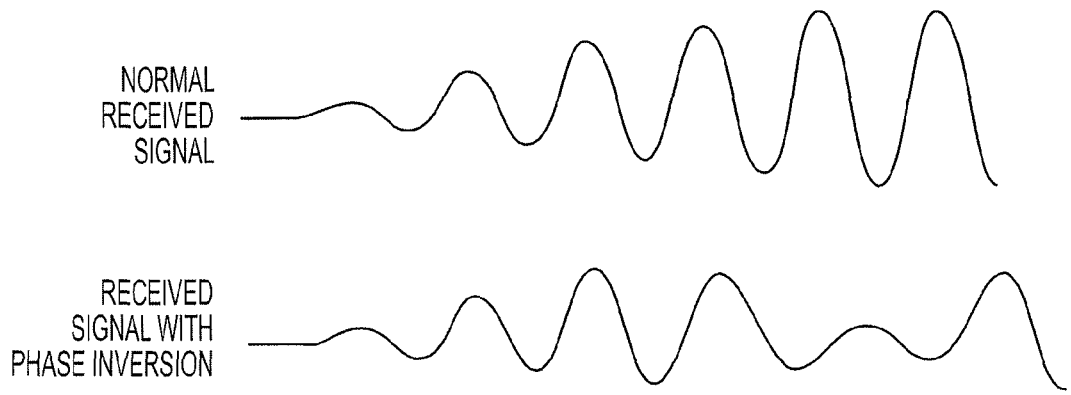
FIG. 36 shows a receiver ultrasonic signal pulse train in accordance with an embodiment of the invention corresponding to the phase inverted transmitter pulse train signal of FIG. 35.
Figure 37:
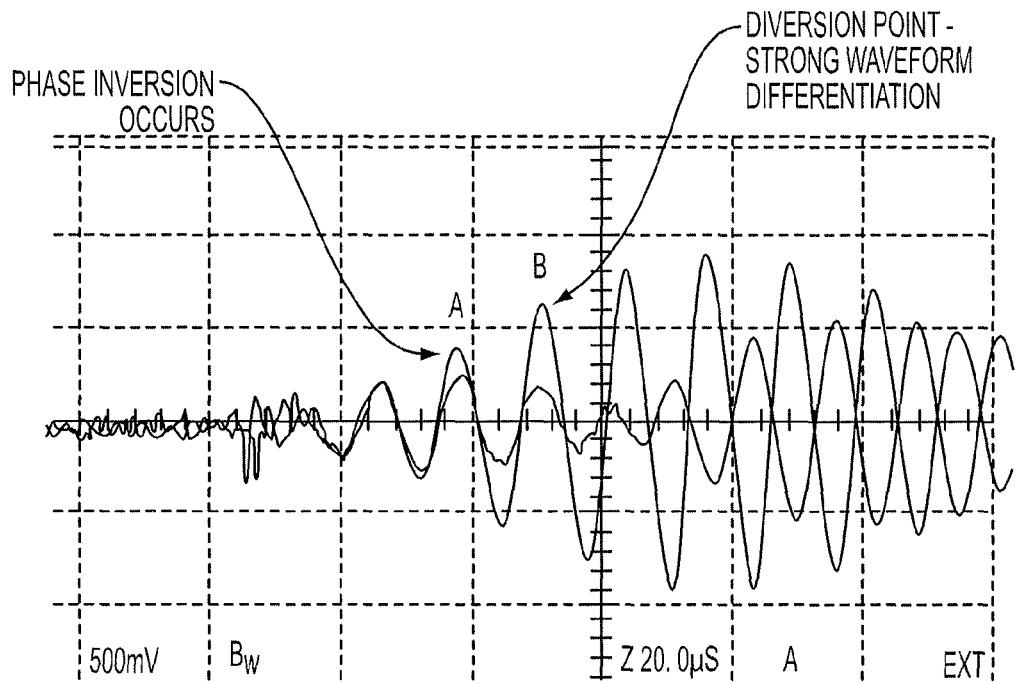
FIG. 37 shows a cathode ray oscilloscope display of received ultrasonic pulse train signals illustrating the superposition of successively normal and phase inverted ultrasonic signal pulse trains in accordance with an embodiment of the invention.
Figure 38:
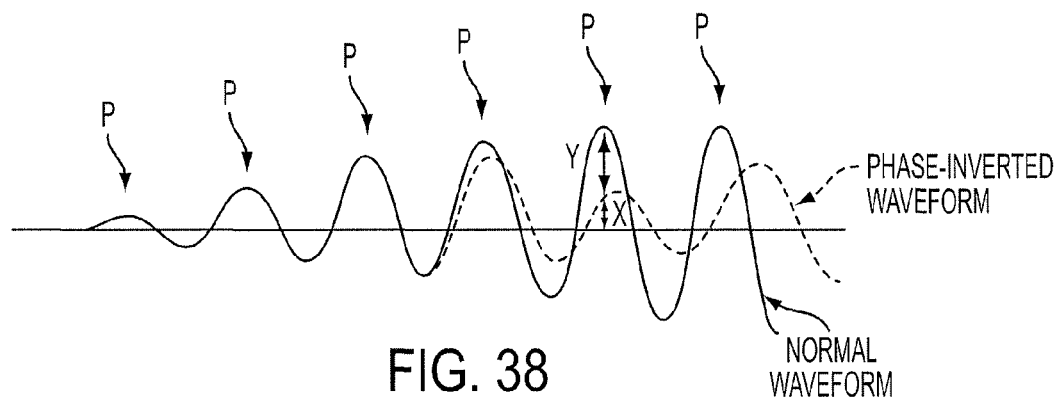
FIG. 38 shows a representation of an example of received normal and phase inverted waveforms used to calculate a diversion point in time for determining the time of arrival of an ultrasonic signal in accordance with an embodiment of the invention.
Figure 39:
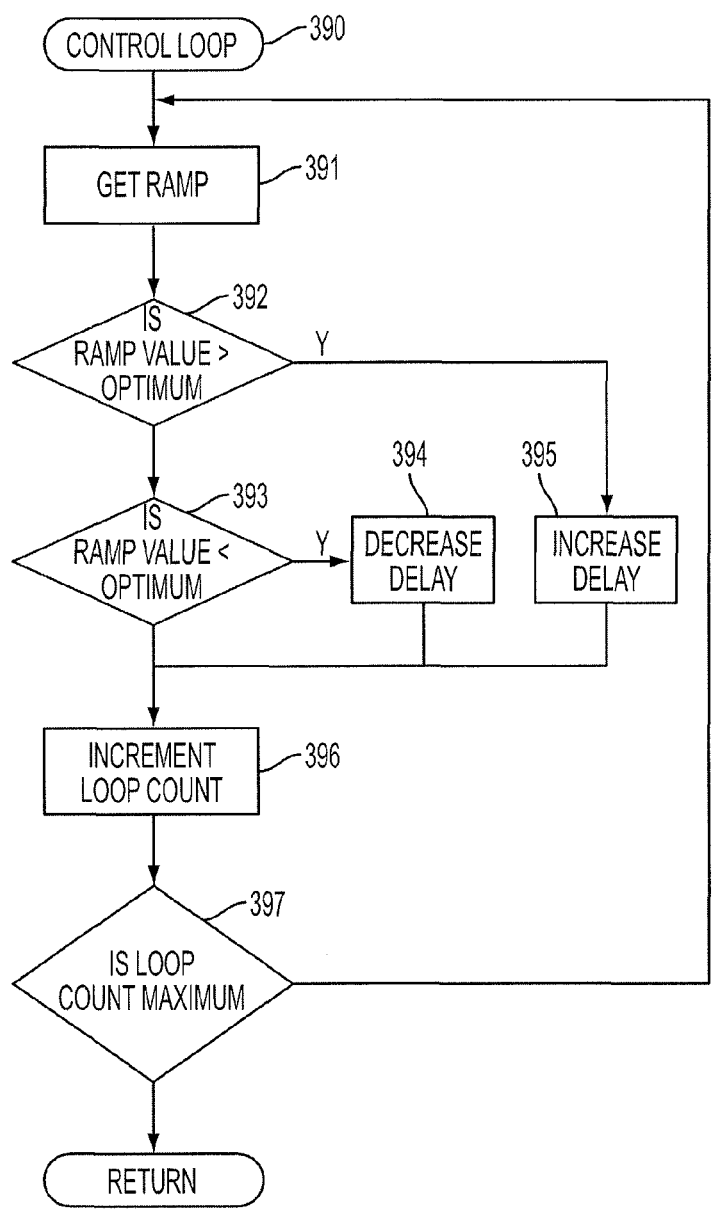
FIG. 39 shows a flow chart for a control loop routine used to adjust a timing delay in the determination of a signal arrival time in accordance with an embodiment of the invention.
Figure 40:
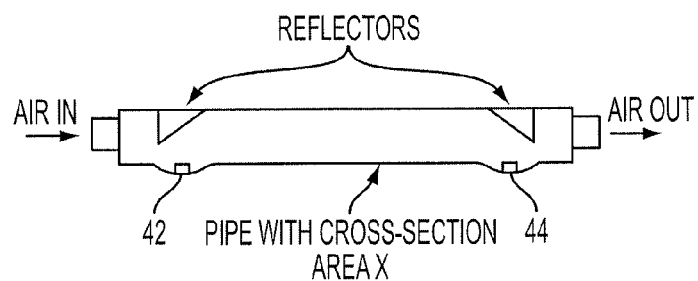
FIG. 40 shows a flow pipe and flow sensor arrangement for illustrating a calculation of flow and speed of sound in accordance with an embodiment of the invention.

The ultrasonic flow sensor 24 relies on being able to accurately measure the time of arrival of a particular target peak or other characteristic wave feature in the received signal. The attributes of the target peak, for example, are that it has sufficient amplitude to provide a good signal-to-noise ratio and that it is not so far into the received pulse train that it can be adversely effected by echoes. For example, one could nominate the fourth or fifth peak for this purpose, The task then, is to reliably locate this peak over a wide range of flows, temperatures and transducer resonances, This is a non-trivial task. For example, threshold methods and envelope curve-fitting methods are not considered to work reliably over temperature and flow variations. The method used in the preferred embodiment described here employs the transmission of a reference signal and a signal which has an artefact introduced into it at a known position in the signal. By comparing the two signals, the position of the artefact may be easily determined. One such artefact is a phase inversion. A phase-inversion signal differs from the normal pulse train in that it has a 180° degree phase shift (i.e. a signal inversion), which may be introduced part way through the pulse train. FIG. 35 illustrates an example of drive waveforms for a first transmitted signal comprising a first normal pulse train and a second transmitted signal comprising a pulse train having the fourth peak with a phase inversion of 180 degrees which is the artefact to be located. FIG. 36 illustrates representations of received waveforms corresponding to the waveforms of FIG. 35. The received signal waveforms differ in shape due to the two different excitations illustrated in FIG. 35. By successively sending normal and phase-inverted signals, it is possible to determine where the artefact occurred, thus identifying a consistent position or marker in the received wave. An actual sample of received signals is shown in FIG. 37. With reference to FIG. 37, it can be seen that there is a marked difference between the two waveforms at peak B. This point is called the diversion point. This is a consistent feature over temperature and flow, provided that the transducers are driven at their resonant frequencies.

Locating the Diversion Point in software.

It is easy to spot the Diversion Point visually. It is also a simple matter to write an algorithm to locate it. With the aid of the received waveform representations of FIG. 38, the algorithm takes the form:

1. Alternately send normal and phase-inverted signals.
2. Scan in time through the received signals.
3. For each peak point P in the normal signal calculate the difference Y between the normal waveform value and the phase-inverted waveform value.
4. If this difference is greater that the phase-inverted value X at that peak point then the diversion point has been found.

The diversion point may be used as the basis for time of flight measurement however it is sometimes desirable to use another location in the waveform. For example, it may be desirable to use the peak after the diversion point. Once the diversion point has been located, the desired timing peak may be found by adding or subtracting a delay time to the time of the diversion point.

Choosing a Peak

In order to accurately determine the transit time of a pulse train, it is necessary to measure the time of occurrence of a known peak in the received signal. For example, it may be required to measure the third or fourth peak after the onset of the received signal. The choice of the peak is a compromise between two conflicting requirements:

1. maximising signal to noise ratio;
2. excluding the effects of higher order modes (basically echoes) which interfere with the received signal.

In order to maximise signal to noise ratio, the chosen peak should be at the point of maximum amplitude. In order to minimise echo effects, the peak chosen should be close to the start of the onset of the received pulse train. In accordance with the preferred embodiment, a good compromise has been to use the fourth peak. This peak appears to consistently have good amplitude while not suffering interference effects.

Homing in on the Desired Peak—ControlLoop( )

Once the lead up to the received waveform has been determined and it is desired to home into the exact position of the fourth peak, a function is called to adjust the timing delay so that the integrator output becomes 50% of it's range. The routine which serves this purpose is ControlLoop( ) designated as 390 in FIG. 39. The routine is given an approximate time of the peak to be tracked (to within ½ a cycle). It launches a pulse train from one transducer and listens at the other. After the prescribed time (approximate time), it enables the integrator (get ramp at step 391) and reads the result which indicates the location of the peak. At step 392, if the integrator value is greater than its mid point, the routine increases the delay at step 394 and re-launches a pulse train. At step 393, if the integrator output is less than 50% it decreases the delay at step 395 and re-launches the pulse train. In this manner, the integrator is made to step towards it 50% mark at which point the routine completes and the resultant delay time is returned to the calling routine.

Calculate Flow and Speed of Sound—CalcFlowAndSound( )

The flow and speed of the ultrasonic signal are determined by measuring forward and reverse transit times using straightforward time-of-flight calculations. A simplified explanation of the method of operation is as follows with reference to FIG. 40. A pulse is sent in two directions. First from sensor A 42, to sensor B 44, and then in the reverse direction, from sensor B to sensor A. Any air flow in the pipe affects the pulse transit time t, the time between launch and reception. In the case where the sound is launched in the direction of the flow, for example, the time of flight is given by:

$$t = \frac{d}{v+s}$$

where t is the transit time, d is the distance between the transmitter and receiver, v is the speed of sound in air and s is the speed of the air between the receiver and transmitter. So, in the case of sensor A transmitting and sensor B receiving, $$t_1 = \frac{d}{v-s}$$

In the reverse case, where sensor B is transmitting and sensor A is receiving, the time of flight is given by:

$$t_2 = \frac{d}{v+s}$$

Manipulating the above two equations, leads to $$v = \frac{d}{2}\left(\frac{1}{t_2} - \frac{1}{t_1}\right)$$

and $$s = \frac{d}{2}\left(\frac{1}{t_2} - \frac{1}{t_1}\right)$$

The volumetric flow f is then simply the speed of the air, s, multiplied by the cross-sectional area A of the pipe. Note that temperature effects are cancelled out in the air speed result. Although the transit times are a function of the speed of sound and therefore are an indirect function of temperature, the equation for s does not require the actual temperature, as long as it is possible to accurately measure the transit times.

Tracking the Wave

The position of the measured wave peak changes with temperature and flow. A flow calculation routine, CalcFlowAndSound( ) comprising calculations as noted above for determining the flow may also incorporate a simple tracking algorithm to lock to a moving peak. The algorithm is very similar to the routine used for ControlLoop( ) as described above in relation to homing in on the desired signal, The error bounds may be slightly relaxed to avoid unnecessary hunting of the waveform peak.

Reporting Transit Times

The flow calculation requires the measurement of the forward and backward transit times of the ultrasonic pulses. The transit time in a flow sensor arrangement of the preferred embodiment is of the order of 350 uSec. In this particular hardware implementation, the transit time measurement in a given direction consists of two parts which must be combined to give the total transit time for that direction. The two parts are:

1. the elapsed time as set by a hardware timer, and
2. a ramp voltage which is proportional to the additional time from the end of that loop count to the occurrence of the centre of a peak in the received ultrasound.

Figure 41:
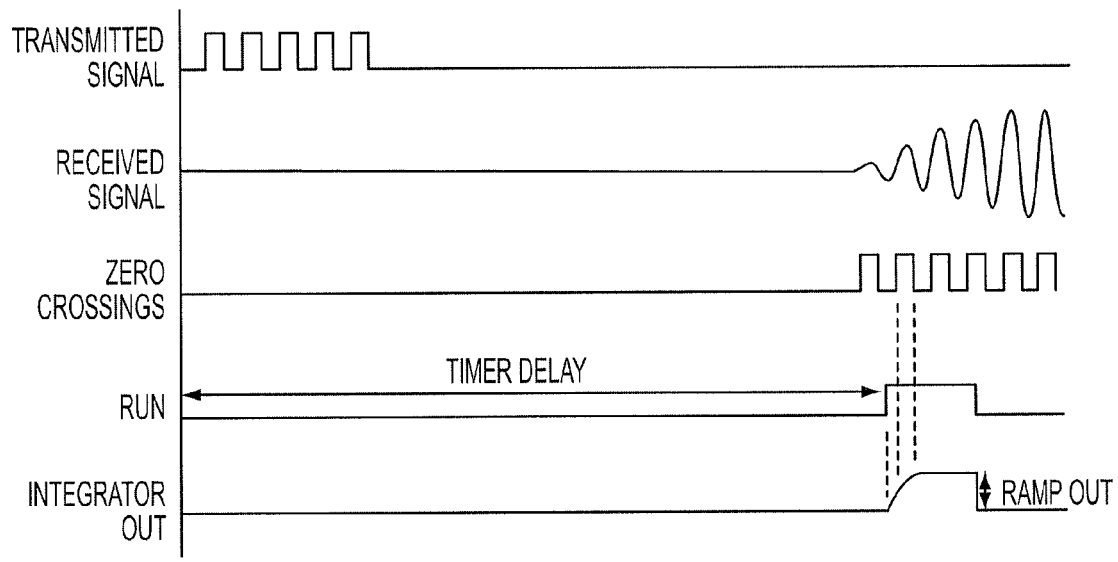
FIG. 41 shows idealised waveforms of a flow sensor system in accordance with an embodiment of the invention.

The waveforms of the flow sensor arrangement corresponding to the above two parts are illustrated in FIG. 41.

Accurately Modelling the Transit Time

As mentioned above, the transit time is measured by the combination of two physical effects. The time elapsed while a hardware timer routine executes and a voltage which is proportional to the additional time from the end of the timer to the middle of a selected peak in the received waveform.

It is important to work in consistent units so we shall measure the transit time in seconds. The transit time equation should therefore be written as follows:

$$t = k1 * \text{countervalue} + c + k2 * (\text{rampout} - k3)$$

where t is the transit time in seconds c is the overhead associated with the timer set up (i.e. the time taken even if timer count were 0)

k1 is the proportionality constant for timer count value (i.e. how many nanoseconds per timer click)

k2 is the proportionality constant for the rampout voltage (i.e. how many nanoseconds it takes for a one volt ramp output change).

k3 is a constant reflecting the fixed offset in the ramp voltage (i.e. the output voltage before ramping begins).

Timer Constants

Timer Constant k1

The timer constants are relatively simply determined and do not vary from unit to unit as long as the same crystal and microprocessor are used. k1 may be determined by inspection taking into account crystal clock frequency and the timer's prescaler value. In the case of the preferred embodiment, the crystal is 16 MHz and the prescaler is 8. The resulting input to the counter is therefore 2 MHz or 500 nSec per tick. This is the k1 value.

Timer Constant c

In practice, the value of c is small enough to be ignored, However, if required, the value of c may be found by experiment. The value of c is the difference between the calculated delay, corresponding to the number of counter ticks, and actual measured delay. This value remains unchanged between units as long as the crystal frequency, microprocessor type and compiler build remains the same. In other words, it is advisable to use the same compiler with the same optimisation options.

Calibrate Ramp

This routine calibrates the relationship between the integrator output and timer counts. In other words, it answers the question, "Where the zero crossing time is fixed, how many volts change in the integrator for each additional delay count?"

Figure 42:
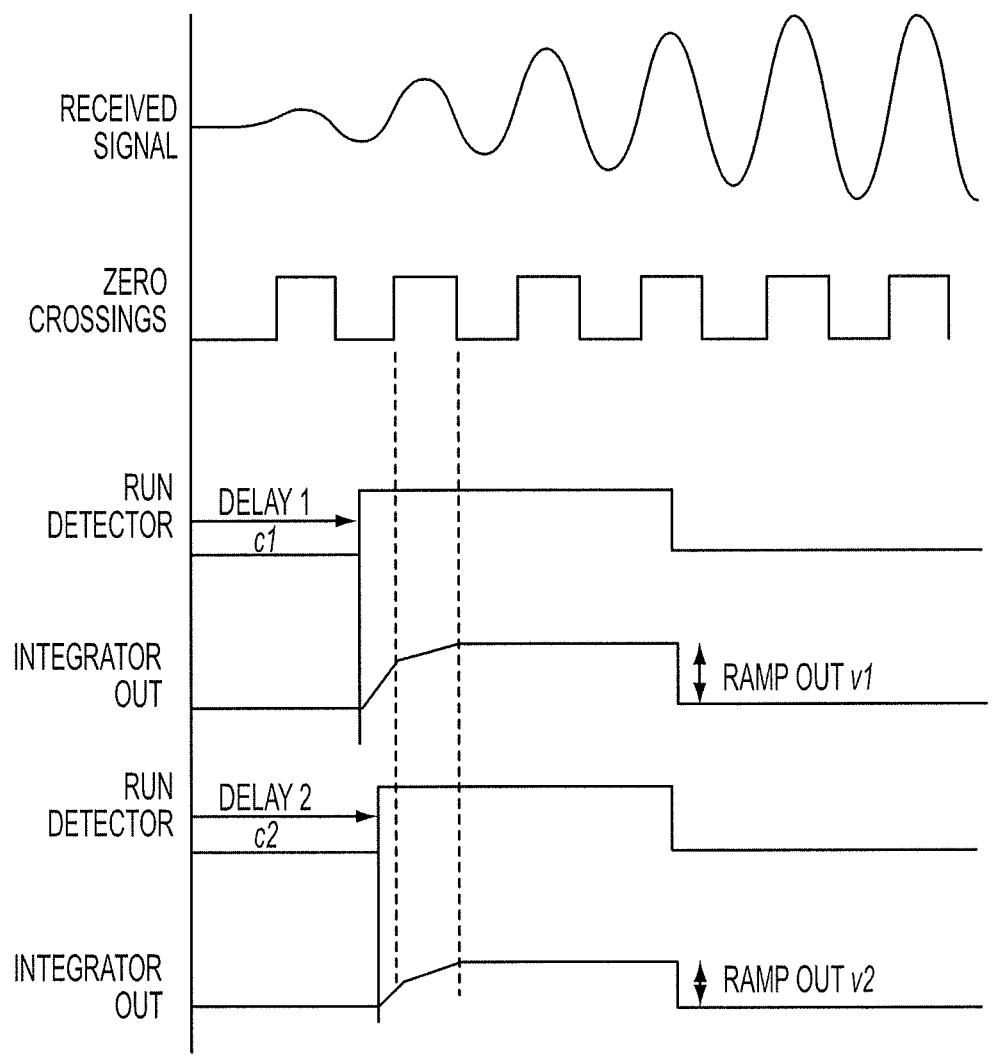
FIG. 42 shows waveforms illustrating the calibration of a dual slope integrator of an embodiment of the invention.

With reference to FIG. 42, for a fixed arrival time of the received signal, the output of the ramp circuit changes as the delay is changed from delay1 to delay2. The relationship is therefore $$k2 = \frac{dv}{dc} = \frac{v2 - v1}{c2 - c1}$$

where v1 is the ramp voltage output at delay1, v2 is the ramp voltage output at delay2, c1 is the software count at delay1 and c2 is the software count at delay2, Error Sources, Timing, It should be noted that absolute flow reading errors or even minor linearity errors are not considered important for the intended application of the flow meter in the preferred embodiment. It is only important that it behave consistently over temperature in order to be stable enough to detect flow changes due to blocked holes in a smoke detector pipe system.

Error in the calculated timing will lead to non-linear flow values. Errors in k1, k2 and k3 will contribute to systematic errors, It is desired that the timing be repeatable to about 30 nSec. Systematic errors larger than this that affect the repeatability of a measurement will cause problems.

Counters

The counters are crystal locked and in this context may be considered to be absolutely accurate. k1, the counter constant, may be determined by inspection and may be considered error free.

Ramp Constants k2 and k3 are used to map ramp voltages to times. It may be shown by simulation that the flow result is not greatly affected by errors in these values as they do not change between timing measurements. Typically, a 10% error in the ramp constant will result in a 0.5% error in the flow reading.

In reality, the calibration process will calibrate the ramp constant to within 1%-2%, causing a flow error at 100 l/m of up to less than 0.2%.

Required ADC Resolution

The analog-to-digital converter in the microcontroller 50 must, after averaging, be able to resolve sufficiently to discriminate timing changes as small as 30 nSec.

Ramp rate 1 is about 0.28 V/uSec

Ramp rate 2 is about 0.14 V/uSec

If the ramp runs for about 14 uSec, for a peak width of about 6 uSec, the average ramp rate will be about (0.28*(14−6)+0.14*6)114=0.22V/uSec.

A 30 nSec time resolution implies a volt resolution of about 0.22*0.03 or about 6 mV. For a 5V reference source, this implies a 10 bit ADC.

In reality, there is sufficient noise in the measurements that significant averaging of repeated measurements is required in order to approach the desired resolution. It may be possible to use a lower resolution converter but the 10 bit variety is readily available at no great cost penalty for the circuit's operation.

Echoes

Echoes may dramatically alter the perceived arrival time of the pulse. They may interfere with the main pulse and cause artificial phase effects.

Echoes are avoided by:

1. Only using the first 5 cycles of the received waveform for timing measurements 2 Allowing a suitable time period (2 mSec) for internal echoes to die away before launching the next ultrasonic pulse train.

Alternate Embodiment

The following description provides an alternative approach to implementing the receiver circuit and encoding algorithms for use in an embodiment of the Ultrasonic Flow Sensor of the present invention. The above described implementation relies on an analog zero-crossing comparator and timing integrator to accurately determine the transit time of the ultrasonic pulse. In this alternate implementation, the received waveform is directly digitised using a fast analog-to-digital converter and the resulting data processed to determine the transit time.

Description of the Electronics

Figure 43:
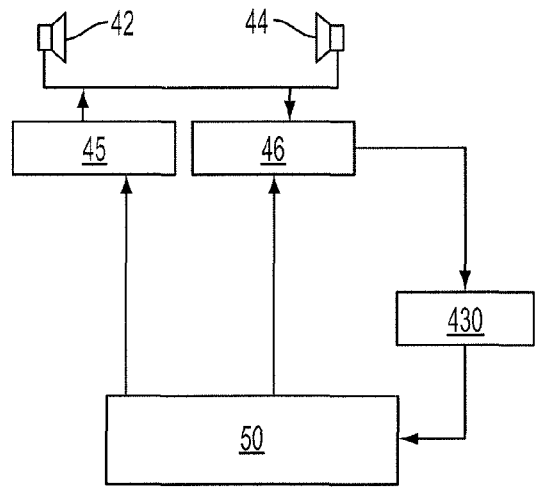
FIG. 43 shows a circuit block diagram of an alternate configuration to that of FIG. 9 of a sensing arrangement in accordance with an alternate embodiment of the invention.

In this alternate implementation the electronics is somewhat simpler that in the above described analog implementation. The two systems may be contrasted by a comparison between the circuit block diagrams of FIG. 9 and FIG. 43. FIG. 43 shows the alternate configuration using an analog-to-digital converter to replace the timing electronics.

Software Implementation

Figure 44:
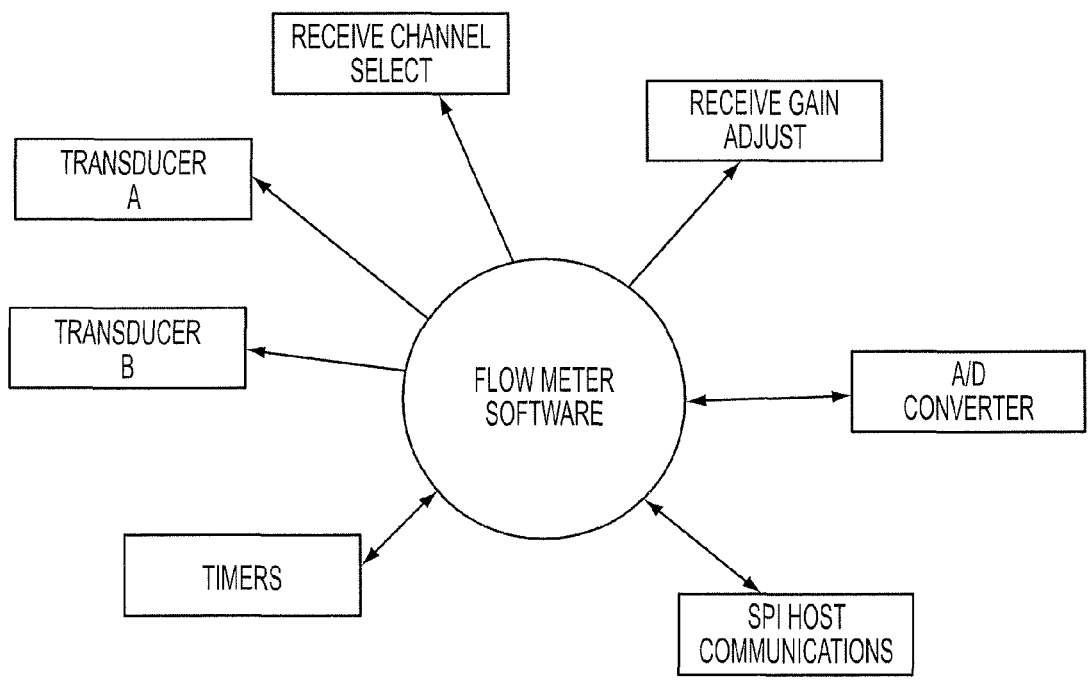
FIG. 44 shows a software context diagram of a flow sensor arrangement in accordance with an alternate embodiment of the invention.

The sampling and analysis process that the software is required to perform using an analog-to-digital front end is described below. For purposes of illustration, a Software Context Diagram is shown in FIG. 44.

Software Method Requirements

As with the above described analog implementation of the preferred embodiment, the software is required to provide the following functions.

Figure 45:
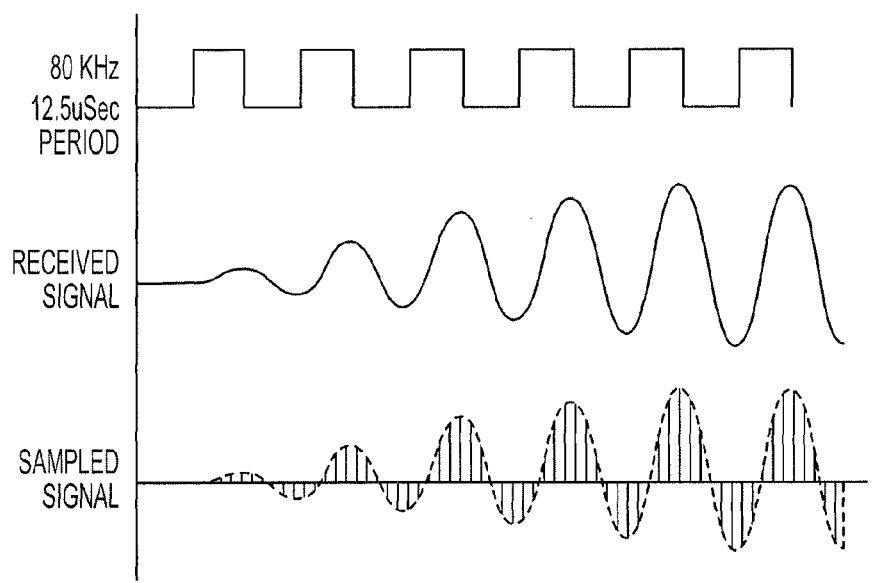
FIG. 45 shows the use of an analog-to-digital (ADC) converter to sample the received ultrasonic signal in accordance with an alternate embodiment of the invention.

1. Adjust gain
2; Determine transducers' resonance frequency
3. Search for received pulses
4, Track changes in the wavefront position
5. Calibrate electronics to account for component variations
6. Store and retrieve parameters in non-volatile storage
7. Communicate with a host
8. Accurately time the arrival of the received signal in each of two directions Digital Sampling In order to perform the above itemised functions using the analog-to-digital front end, it is necessary to sample the received signal. This process is visualised diagrammatically in the waveform representations of FIG. 45.

The fundamental measurements required to implement the flow sensor algorithms are as follows:

1. Measurement of signal DC level prior to waveform arrival.
2. Peak amplitude of the waveform in the area of interest (eg, first 10 cycles)
3. Recording of first and second characteristic signals in order to determine the point of diversion
4. Calculation of zero-crossing points on each side of the peak of interest.

Storing the Waveform

Figure 46:
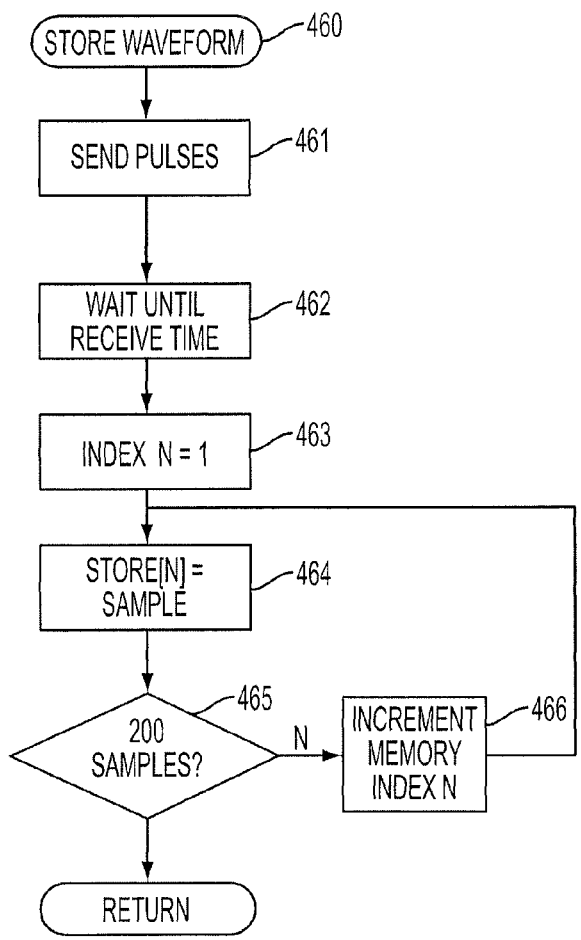
FIG. 46 shows a flow chart of a routine for storing the sampled received signal into memory for later processing in accordance with an alternate embodiment of the invention.

Although it is possible to perform all of the required calculations as the received signal data are sampled, it is generally considered easier to sample the waveform into memory and examine the data thereafter. The required processing power is less if this is done, and therefore likely to be a lower-cost solution, but either approach is acceptable. Nonetheless, it is noted that real time evaluation of all of the routines mentioned is possible but requires the use of a powerful DSP or equivalent gate array. In order to target reduced cost of good, the preferred implementation required the waveform be sampled into memory. FIG. 46 shows a flow chart of a routine for designated as Store Waveform 460, Pulses are sent at step 461 and an appropriate wait time is executed at step 462. A memory index is set to its start value at step 463. Sampled values of the received waveform are stored at step 464. The memory index is incremented for each stored sample at step 466 until 200 samples are stored, step 465. It is considered sufficient to store 200 samples as this is equivalent to about 16 cycles of the 80 kHz ultrasonic signal.

Base Function Routines to Replace Electronics in Analog Implementation

The analogue electronics in the preferred embodiment of the flow sensor system provided the following functions:

1. DC level
2. Peak value detection
3. Zero crossing detection
4. Peak centre location The software routines implemented to perform these functions are now described.

Measurement of the DC Level

Figure 47:
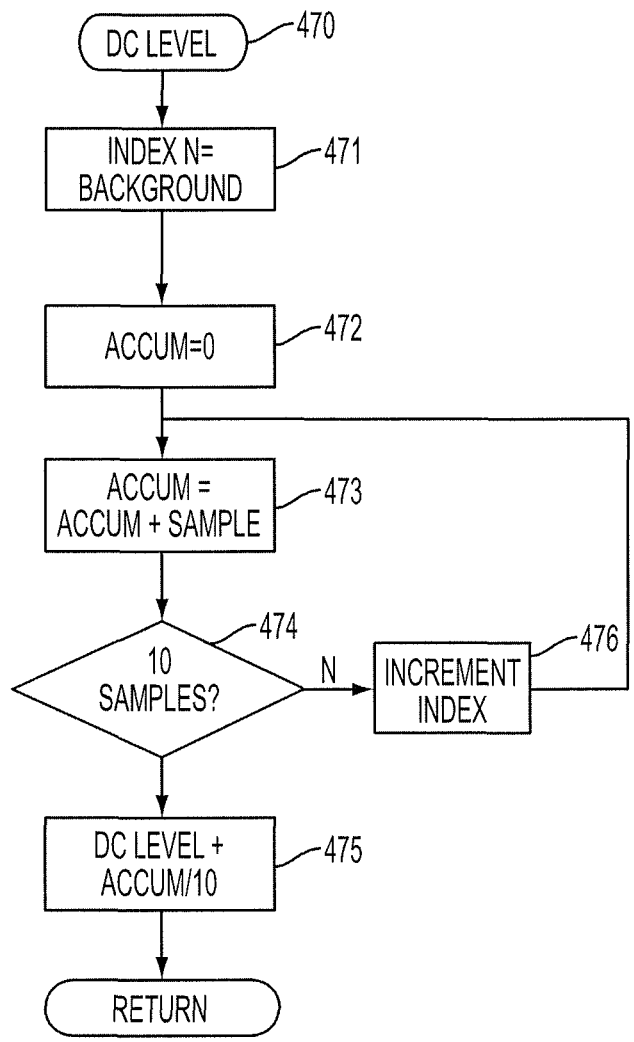
FIG. 47 shows a flow chart of a routine for determining a voltage reference against which to compare the sampled signal in accordance with an alternate embodiment of the invention.

In order to determine the positions of the zero crossings on each side of a peak, it is necessary to establish a voltage reference against which to compare the sampled waveform. FIG. 47 shows a routine designated as DC Level 470 for performing this function. This routine examines the stored, received signal prior to the onset of the first peak to establish the idle or DC level against which the rest of the waveform is to be compared. At step 471 an index is set to a background level prior to the first peak of the received waveform and a sample accumulator is cleared (initialised) at step 472. Sample values are accumulated until a maximum of 10 samples are accumulated at steps 473, 474 and 476. A DC level is determined at step 475 by averaging the accumulated samples.

Peak Value

Figure 48:
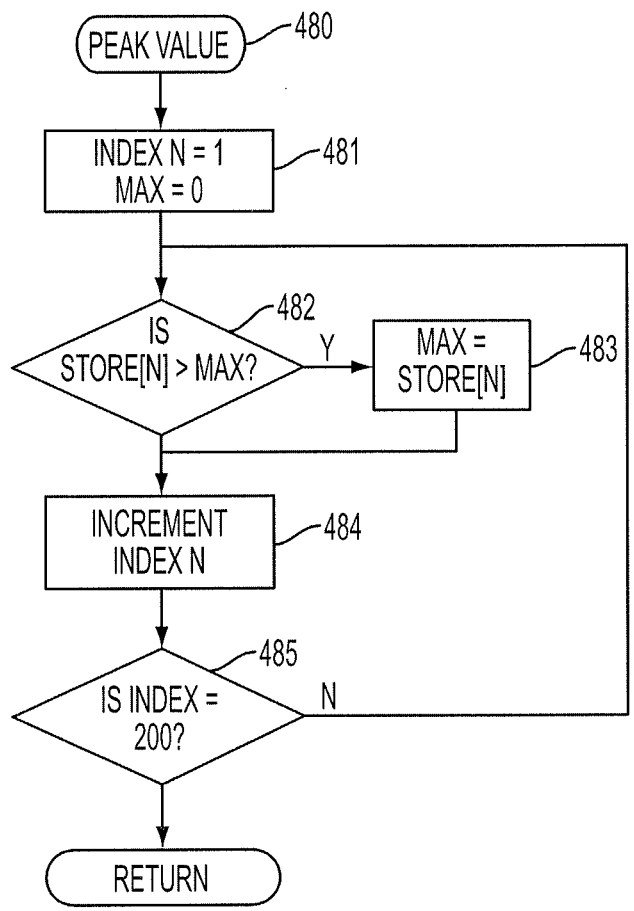
FIG. 48 shows a flow chart of a routine for determining a peak value of the received and sampled signal in accordance with an alternate embodiment of the invention.

A routine, designated as Peak Value 480 in FIG. 48, determines the peak value of the received signal over a region of interest. This routine is useful in optimising the receiver gain. At step 281 a memory index is set to a start value and a max value corresponding to a peak value is initialised. The loop at steps 482, 483 and 484 increments the index each time a sampled value exceeds the value of max. Step 485 restricts the routine to processing 200 samples and the peak value is returned in the variable max.

Zero-Crossing Detection

Figure 49:
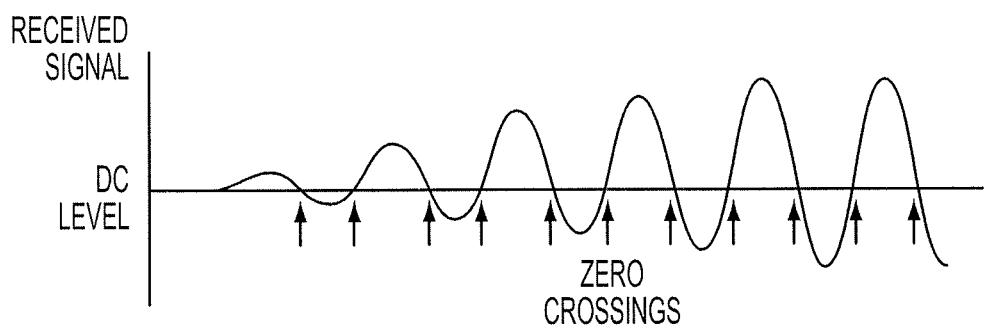
FIG. 49 is a waveform illustration of a referenced DC level and zero-crossing points of the received and sampled signal in accordance with an alternate embodiment of the invention.
Figure 50:
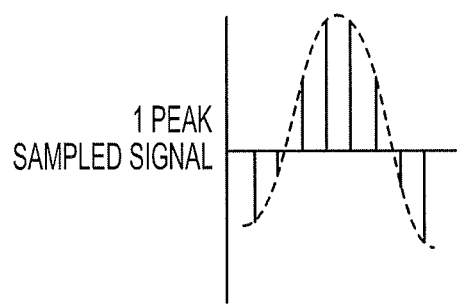
FIG. 50 is a magnified view of a single sampled peak of the received signal in accordance with an alternate embodiment of the invention.
Figure 51:
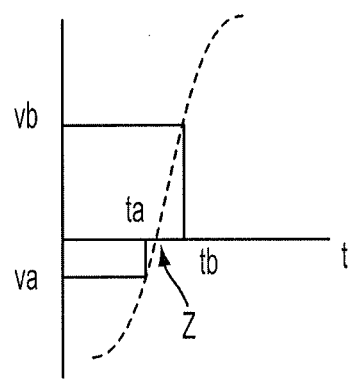
FIG. 51 illustrates sample points on either side of a zero-crossing of the received signal in accordance with an alternate embodiment of the invention.

A zero crossing is defined to occur where the signal makes a transition from below the above determined DC level to above it or from above the DC level to below. The DC level and the zero crossing points of the received signal are shown in FIG. 49. FIG. 50 is a magnified view of one sampled peak in the received signal. It can be seen that a zero crossing may be identified by a transition of the waveform from below the DC level to above it, or from above the DC level to below. The precise location of the zero crossing point, in terms of its time of occurrence, may be calculated by interpolation, Referring to FIG. 51, which shows sample points on either side of a zero crossing, if sample value va is below the DC level and sample value vb is above, then the time position t of the zero crossing Z may be simply calculated by:

$$tz = ta + va\frac{tb - ta}{vb - va}$$

Peak Centre Location

Figure 52:
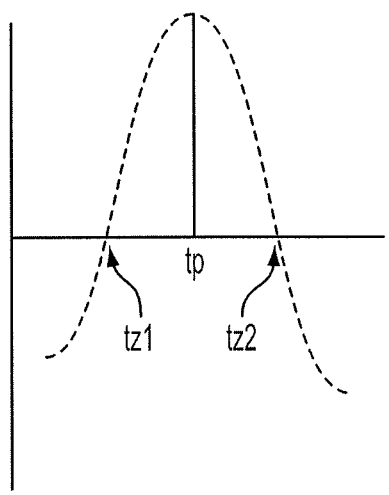
FIG. 52 illustrates the location of a peak centre within the received and sampled signal in accordance with an alternate embodiment of the invention.

Referring to FIG. 52, once the zero-crossing points on either side of a peak tz1 and tz2 have been located, it is a simple matter to calculate the location of the centre of the peak tp, as follows. Assuming that the peak is symmetrical about its peak value, then $$tp = \frac{tz1 + tz2}{2}$$

The routines and methods described above may be used to replace some analog circuitry on the ultrasonic flow sensor in accordance with an alternate embodiment of the invention. These routines and methods may feed into the analog routines described above providing raw data which is presently available through the use of analog circuitry.

The purely digital, sampled approach has the benefit of reduced hardware complexity as well as a possible reduction in cost of goods as analog-to-digital converters and high-speed processors drop in price.

While this invention has been described in connection with specific embodiments thereof, it will be understood that it is capable of further modification(s). This application is intended to cover any variations uses or adaptations of the invention following in general, the principles of the invention and comprising such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures. For example, although a nail and a screw may not be structural equivalents in that a nail employs a cylindrical surface to secure wooden parts together, whereas a screw employs a helical surface to secure wooden parts together, in the environment of fastening wooden parts, a nail and a screw are equivalent structures.

"Comprises/comprising" when used in this specification is taken to specify the presence of stated features, integers, steps or components but does not preclude the presence or addition of one or more other features, integers, steps, components or groups thereof.

The invention claimed is:

1. A method of detecting one or more blocked sampling holes in a pipe of an aspirated smoke detector system, said aspirated smoke detector system comprising a sampling network including one or more pipes having sampling holes, an aspirator for drawing air through the sampling network to a detector; and a flow sensor, said method comprising:
   ascertaining the base flow of fluid through a particle detector using the flow sensor;
   monitoring subsequent flow through the particle detector using the flow sensor; and
   comparing in a processor, the subsequent flow with the base flow, and determining that one or more sampling holes of the sampling network are blocked and indicating a fault, if the difference between the base flow and the subsequent flow exceeds a predetermined threshold.

2. The method of claim 1 wherein the flow sensor is an ultrasonic flow sensor.

3. The method of claim 1, wherein the difference between base flow and subsequent flow is compared over a length of time.

4. The method of claim 1 wherein the flow is determined according to the following general flow calculation:

$$f = s \times A$$

where f=volumetric flow;
A=cross sectional area of an air flow path through the detector system;
s=speed of air through the detector system such that s is given by;

$$s = \frac{d}{2}\left(\frac{1}{t_2} - \frac{1}{t_1}\right)$$

where $t_1$ is the transit time of a signal transmitted in a forward direction, being generally in the direction of flow, from a first transducer located adjacent the flow path to a second transducer located generally opposite the first transducer and adjacent the flow path;
$t_2$ is the transit time of a signal transmitted in a reverse direction, being generally against the direction of flow, from the second transducer to the first transducer; and
d is a distance travelled by the signal between the first and second transducer; and wherein both $t_1$ and $t_2$ are determined.

5. A non-transitory computer readable medium encoded with a computer program containing instructions stored thereon for causing a computer processor to control a particle detector to perform a method comprising the steps of:
   ascertaining the base flow of fluid through a particle detector using a flow sensor;
   monitoring subsequent flow through the particle detector using the flow sensor; and
   comparing in a processor, the subsequent flow with the base flow, and determining that one or more sampling holes of the sampling network are blocked and indicating a fault, if the difference between the base flow and the subsequent flow exceeds a predetermined threshold.

6. The non-transitory computer readable medium as claimed in claim 5, wherein in the method, the difference between base flow and subsequent flow is compared over a length of time.

7. The non-transitory computer readable medium as claimed in claim 5, wherein in the method, the flow is determined according to the following general flow calculation:

$$f = s \times A$$

where f=volumetric flow;
A=cross sectional area of an air flow path through the detector system;
s=speed of air through the detector system such that s is given by;

$$s = \frac{d}{2}\left(\frac{1}{t_2} - \frac{1}{t_1}\right)$$

where $t_1$ is the transit time of a signal transmitted in a forward direction, being generally in the direction of flow, from a first transducer located adjacent the flow path to a second transducer located generally opposite the first transducer and adjacent the flow path;
$t_2$ is the transit time of a signal transmitted in a reverse direction, being generally against the direction of flow, from the second transducer to the first transducer; and
d is a distance travelled by the signal between the first and second transducer; and wherein both $t_1$ and $t_2$ are determined.

8. A non-transitory computer readable medium encoded with a computer program containing instructions stored thereon for causing a computer processor to control a particle detector to perform a method comprising the steps of:

ascertaining the base flow of fluid through a particle detector using an ultrasonic flow sensor:

monitoring subsequent flow through the particle detector using the ultrasonic flow sensor; and comparing in a processor, the subsequent flow with the base flow, and determining that one or more sampling holes of the sampling network are blocked and indicating a fault, if the difference between the base flow and the subsequent flow exceeds a predetermined threshold.

9. An aspirated smoke detector comprising:

a particle detector, a sampling network including one or more pipes with one or more sampling holes through which samples enter the one or more pipes; and an aspirator for drawing an air sample through the sampling network to the particle detector;

wherein the aspirated smoke detector includes an ultrasonic flow sensor arranged to detect the flow rate of air entering the particle detector, and wherein the aspirated smoke detector further comprises a processor configured to:

ascertain the base flow of fluid through the particle detector using the flow sensor;

monitor subsequent flow through the particle detector using the flow sensor; and compare the subsequent flow with the base flow, and determine that one or more sampling holes of the sampling network are blocked and indicate a fault, if the difference between the base flow and the subsequent flow exceeds a predetermined threshold.

* * * * *